US010611998B2

(12) United States Patent
Keirstead et al.

(10) Patent No.: US 10,611,998 B2
(45) Date of Patent: Apr. 7, 2020

(54) OLIGODENDROCYTES DERIVED FROM HUMAN EMBRYONIC STEM CELLS FOR REMYELINATION AND TREATMENT OF SPINAL CORD INJURY

(75) Inventors: Hans S. Keirstead, Irvine, CA (US);
Gabriel I. Nistor, Placentia, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 964 days.

(21) Appl. No.: 12/357,244

(22) Filed: Jan. 21, 2009

(65) Prior Publication Data

US 2009/0232779 A1 Sep. 17, 2009

Related U.S. Application Data

(60) Division of application No. 11/637,632, filed on Dec. 11, 2006, now Pat. No. 7,579,188, which is a continuation of application No. 10/661,105, filed on Sep. 12, 2003, now abandoned, which is a continuation of application No. PCT/IB03/03539, filed on Jul. 11, 2003, which is a continuation-in-part of application No. 10/406,817, filed on Apr. 4, 2003, now Pat. No. 7,285,415.

(60) Provisional application No. 60/395,382, filed on Jul. 11, 2002.

(51) Int. Cl.
*C12N 5/0735* (2010.01)
*C12N 5/0797* (2010.01)
*C12N 5/079* (2010.01)
*A61K 35/12* (2015.01)

(52) U.S. Cl.
CPC ......... *C12N 5/0622* (2013.01); *C12N 5/0606* (2013.01); *C12N 5/0623* (2013.01); *A61K 35/12* (2013.01); *C12N 2501/115* (2013.01); *C12N 2501/395* (2013.01); *C12N 2503/02* (2013.01); *C12N 2506/02* (2013.01)

(58) Field of Classification Search
CPC ... C12N 5/0606; C12N 5/0622; C12N 5/0623
See application file for complete search history.

(56) References Cited

U.S. PATENT DOCUMENTS

| | | | |
|---|---|---|---|
| 5,654,183 A | 8/1997 | Anderson et al. | |
| 5,750,376 A | 5/1998 | Weiss et al. | |
| 5,753,506 A | 5/1998 | Johe | |
| 5,766,948 A | 6/1998 | Gage et al. | |
| 5,830,621 A | 11/1998 | Suzuki et al. | |
| 5,849,553 A | 12/1998 | Anderson et al. | |
| 5,851,832 A | 12/1998 | Weiss et al. | |
| 5,928,947 A | 7/1999 | Anderson et al. | |
| 5,968,829 A | 10/1999 | Carpenter | |
| 6,040,180 A | 3/2000 | Johe | |
| 6,090,622 A | 7/2000 | Gearhart et al. | |
| 6,200,806 B1 | 3/2001 | Thomson | |
| 6,235,527 B1 * | 5/2001 | Rao et al. | 435/325 |
| 6,235,537 B1 | 5/2001 | North et al. | |
| 6,238,922 B1 | 5/2001 | Uchida | |
| 6,245,564 B1 | 6/2001 | Goldman et al. | |
| 6,458,589 B1 * | 10/2002 | Rambhatla et al. | 435/370 |
| 6,887,706 B2 | 5/2005 | Zhang et al. | |
| 6,900,054 B2 * | 5/2005 | Rao | C12N 5/0622 435/368 |
| 7,285,415 B2 | 10/2007 | Keirstead et al. | |

FOREIGN PATENT DOCUMENTS

| | | |
|---|---|---|
| CA | 2253078 | 10/1998 |
| WO | 97/07200 | 2/1997 |
| WO | 97/32608 | 9/1997 |
| WO | 98/50526 | 11/1998 |
| WO | 99/01159 | 1/1999 |
| WO | 99/20741 | 4/1999 |
| WO | 00/23571 | 4/2000 |
| WO | 01/28342 | 4/2001 |
| WO | 01/51610 | 7/2001 |
| WO | 01/68815 | 9/2001 |
| WO | 01/88104 | 11/2001 |
| WO | 01/98463 | 12/2001 |
| WO | 2003/000868 | 1/2003 |

OTHER PUBLICATIONS

Reubinoff et al., Neural progenitors from human embryonic stem cells. Nature Biotechnology 2001;19 (12):1134-40.
Scolding et al., Oligodendrocyte progenitors are present in the normal adult human CNS and in the lesions of multiple sclerosis. Brain 1998;121:2221-8.
Scolding et al., Identification of A2B5-positive putative oligodendrocyte progenitor cells and A2B5-positive astrocytes in adult human white matter. Neuroscience 1999;89(1):1-4.
Svendsen et al., A new method for the rapid and long term growth of human neural precursor cells. J. Neurosci. Meth. 1998;85:141-52.
Thomson et al., Neural differentiation of rhesus embryonic stem cells. APMIS 1998;106:149-57.
Thomson et al., Embryonic stem cell lines derived from human blastocysts. Science 1998;282(5391):1145-7.

(Continued)

*Primary Examiner* — Robert C Hayes
(74) *Attorney, Agent, or Firm* — Shweta Chandra; Bozicevic, Field & Francis LLP

(57) ABSTRACT

This invention provides populations of neural cells bearing markers of glial cells, such as oligodendrocytes and their precursors. The populations are generated by differentiating pluripotent stem cells such as human embryonic stem cells under conditions that promote enrichment of cells with the desired phenotype or functional capability. Various combinations of differentiation factors and mitogens can be used to produce cell populations bearing markers of oligodendrocyte precursor cells. Upon further differentiation form complex processes characteristic of mature oligodendrocytes. The cells are capable of forming myelin sheaths, and can be used therapeutically improve function of the central nervous system.

16 Claims, 20 Drawing Sheets

(56) References Cited

OTHER PUBLICATIONS

Wilson, Human oligodendrocyte precursor cells in vitro: phenotypic analysis and differential response to growth factors. Glia 2003;44:153-65.
Wohl, Retinoic acid enhances neuronal proliferation and astroglial differentiation in cultures of CNS stem cell-derived precursors. Journal of Neurobiology 1998;37(2):281-90.
Xian et al., A subset of ES-cell-derived neural cells marked by gene targeting. Stem Cells 2003;21:41-9.
Xu et al., Feeder-free growth of undifferentiated human embryonic stem cells. Biotechnol. 2001;19:971-4.
Zhang et al., Adult brain retains the potential to generate oligodendroglial progenitors with extensive myelination capacity. PNAS 1999;96:4089-94.
Zhang et al., In vitro differentiation of transplantable neural precursors from human embryonic stem cells. Nature Biotech. 2001;19:1129-33.
China J. Orthop Trauma 2000;2(4):329-31.
Akiyama et al., Remyelination of the rat spinal cord by transplantation of identified bone marrow stromal cells. J. Neurosci. 2002;22(15):6623-30.
Arsenijevic et al., Isolation of multipotent neural precursors residing in the cortex of the adult human brain. Exp. Neuro. 2001;170:48-62.
Bain et al, Expression of retinoid X receptors in P19 embryonal carcinoma cell and embryonic stem cells. Biochem. Biophys. Res. Comm. 1994;200(3):1252-56.
Bain et al., From embryonal carcinoma cells to neurons: The P19 pathway. Bioessays 1994;16(5):343-8.
Bain et al., Embryonic stem cells express neuronal properties in vitro. Developmental Biology 1995;168:342-57.
Bain et al., Neural cells derived by in vitro differentiation of P19 and embryonic stem cells. Perspectives on Developmental Neurobiology 1998;5:175-8.
Barres et al., Cell death and control of cell survival in the oligodendrocyte lineage. Cell 1992;70(1):31-46.
Barres et al., A novel role from thyroid hormone, glucocorticoids and retinoic acid in timing oligodendrocyte development. Development 1994;120:1097-108.
Billon et al., Normal timing of oligodendrocyte development from genetically engineered, lineage-selectable mouse ES cells. J. Cell Sci. 2002;115:3657-65.
Bjorklund et al., Embryonic stem cells develop into functional dopaminergic neurons after transplantation in a Parkinson rat model. PNAS 2002;99(4):2344-2349.
Blakemore et al., The origin of remyelinating cells in the central nervous system. J. Neuroimmunology 1999;98:69-76.
Bottenstein. Growth requirements in vitro of oligodendrocyte cell lines and neonatal rat brain oligodendrocytes. PNAS 1986;83(6):1955-9.
Brustle et al., In vitro-generated neural precursors participate in mammalian brain development. PNAS 1997;94:14809-14.
Brustle et al., Embryonic stem cell-derived glial precursors: A source of myelinating transplants. Science 1999;285:754-6.
Carpenter et al., Enrichment of neurons and neural precursors from human embryonic stem cells. Exp. Neurology 2001;172:383-97.
Chandross et al., Tracking oligodendrocytes during development and regeneration. Microsci. Res. Tech. 2001;52 (6):766-77.
Chen et al., Gene transfer and expression in oligodendrocytes under the control of myelin basic protein transcriptional control region mediated by adeno-associated virus. Gene Ther. 1998;5(1):50-8.
Eccleston et al., The differentiation of oligodendrocytes in a serum-free hormone-supplemented medium. Brain Res. 1984;318(1):1-9.
Fraichard et al., In vitro differentiation of embryonic stem cells into glial cells and functional neurons. J. Cell. Sci. 1995;108:3181-8.
Freed, Will embryonic stem cells be a useful source of dopamine neurons for transplant into patients with Parkinson's Disease?. PNAS 2002;99:1755-7.
Gottlieb et al., An in vitro pathway from embryonic stem cells to neurons and glia. Cells Tissues Organs 1999;165 (3-4):165-72.
Gu et al., Selenium is required for normal upregulation of myelin genes in differentiation onligodendrocytes. J. Neurosci. Res. 1997;47(6):626-35.
Guan et al., Embryonic stem cell-derived neurogenesis. Retinoic acid induction and lineage selection of neuronal cells. Cell Tissue Res. 2001;305(2):171-6.
Hajihosseini et al., Origin of oligodendrocytes within the human spinal cord. J. Neurosci. 1996;16(24):7981-94.
Hinks et al., Depletion of endogenous oligodendrocyte pogenitors rather than increased availability of survival factors is a likely explanation for enhanced survival of transplanted oligodendrocyte progenitors in X-irradiated compared to normal CNS. Neuropath. Appl. Neurobio. 2001;27:59-67.
Holland. Giomagenesis: Genetic alterations and mouse models. Nat. Rev. Genet. 2001;2(2):120-9.
Kalman et al., Spectrum and classification of inflammatory demyelinating diseases of the central nervous system. Curr. Neurology and Neurosci. Reports 2001;1:249-56.
Keirstead et al., In vivo immunological suppression of spinal cord myelin development. Brain Res. Bulletin 1997;44(6):727-34.
Keirstead et al., Identification of post-mitotic oligodendrocytes incapable of remyelination within the demyelinated adult spinal cord. J. Neuropath. Exp. Neurology 1997;56(11):1191-1201.
Keirstead et al., A quantifiable model of axonal regeneration in the demyelinated adult rat spinal cord. Exp. Neurol. 1998;151:303-13.
Keirstead et al., Response of the oligodendrocyte progenitor cell population (defined by NG2 labelling) to demyelination of the adult spinal cord. GLIA 1998;22:161-70.
Keirstead et al., The role of oligodendrocytes and oligodendrocyte progenitors in CNS remyelination. Adv. Exp. Med. Biol. 1999;468:183-97.
Keirstead et al., Polysialylated neural cell adhesion melecule-positive CNS precursors generate both oligodendrocytes and schwann cells to remyelinate the CNS after transplantation. J. Neurosci. 1999;19(17):7529-36.
Keirstead et al., Enhanced axonal regeneration following combined demyelination plus schwann cell transplantation therapy in the injured adult spinal cord. Exp. Neurol. 1999;159(1):225-36.
Keirstead. Stem cell transplantation into the central nervous system and the control of differentiation. J. Neurosci. Res. 2001;63:233-6.
Kornblum et al., Molecular markers in CNS stem cell research: Hitting a moving target. Nature Reviews 2001;2:843-6.
Kuo et al., Differentiation of monkey embryonic stem cells into neural lineages. Biol. Reprod. 2003;68:1727-35.
Lee et al., Efficient generation of midbrain and hindbrain neurons from mouse embryonic stem cells. Nature Biotech. 2000;18:675-8.
Li et al., Generation of purified neural precursors from embryonic stem cells by lineage selection. Curr. Bio. 1998;8:971-4.
Lie et al., The adult substantia nigra contains progenitor cells with neurogenic potential. J. Neurosci. 2002;22 (15):6639-49.
Liu et al., Embryonic stem cells differentiate into oligodendrocytes and myelinate in culture and after spinal cord transplantation. PNAS 2000;97(11):6126-31.
McDonald et al., Transplanted embryonic stem cells survive, differentiate and promote recovery in injured rat spinal cord. Nature Med. 1999;5(12):1410-12.
McDonald et al., Repairing the damaged spinal cord. Scientific American 1999;281(3):64-73.
Mujtaba et al., Lineage-restricted neural precursors can be isolated from both the mouse neural tube and cultured ES cells. Dev. Bio. 1999;214:113-27.
Nishiyama et al., Co-localization of NG2 proteoglycan and PDGF alpha-receptor on O2A progenitor cells in the developing rat brain. J. Neurosci. Res. 1996;43:299-314.
Nistor et al., Induction of high purity oligodendrocyte cultures from human embryonic stem cells. Biosciences Information Services, Philadelphia, PA US 2002;2002: Abstract 726.16.
O'Shea, Neuronal differentiation of mouse embryonic stem cells: Lineage selection and forced differentiation paradigms. Blood Cells, Molecules and Diseases 2001;27(3):705-12.
Ostenfeld et al., Regional specification of rodent and human neurospheres. Brain Res. Dev. 2002;134(1-2):43-55.

(56) References Cited

OTHER PUBLICATIONS

Pardo et al., Differentiation of rat striatal embryonic stem cells in vitro: Monolayer culture vs. three-dimensional coculture with differentiated brain cells. J. Neurosci. Res. 2000;59(4):504-12.

Park et al., Transplantation of neural progenitor and stem cells: Developmental insights may suggest new therapies for spinal cord and other CNS dysfunction. J. Neurotrauma 1999;16(8):675-87.

Blakemore et al., "Transplanted Glial Cells Migrate Over a Greater Distance and Remyelinate Demyelinated Lesions More Rapidly Than Endogenous Remyelinating Cells," Journal of Neuroscience Research, 2000, vol. 61, pp. 288-294.

Murray, et al (1997) "Emergence of oligodendrocytes from human neural spheres." *J. Neurosci. Res.* 50:146-156.

Zhang, et al (2000) "Tracing human oligodendroglial development in vitro" *J. Neurosci. Res.* 59:421-429.

Janabi et al. (1999) "Negative Feedback Between Prostaglandin and α- and β-Chemokine Synthesis in Human Microglial Cells and Astrocytes" J Immunol 162(3)1701-1706.

Serguera et al. (2001) "Primary Adult Human Astrocytes as an ex Vivo Vehicle for β-Glucuronidase Delivery in the Brain" Mol Ther 3(6):875-881.

Zwaka, et al., "A germ cell origin of embryonic stem cells?", Development 132, pp. 227-233, 2005.

\* cited by examiner

OLIGODENDROCYTES DERIVED FROM HUMAN EMBRYONIC STEM CELLS FOR REMYELINATION AND TREATMENT OF SPINAL CORD INJURY

CROSS-REFERENCE TO RELATED APPLICATIONS

This application is a divisional of U.S. application Ser. No. 11/637,632, filed Dec. 11, 2006, which is a continuation of U.S. application Ser. No. 10/661,105, filed Sep. 12, 2003, now abandoned, which application is a continuation of PCT application serial no. PCT/IB2003/003539, filed Jul. 11, 2003, entitled "Oligodendrocytes Derived from Human Embryonic Stem Cells fro Remyelination and Treatment of Spinal Cord Injury," which application was filed in English and designating the United States, and a continuation-in-part of U.S. application Ser. No. 10/406,817, filed Apr. 4, 2003, issued as U.S. Pat. No. 7,285,415 on Oct. 23, 2007, which application claims the benefit of U.S. provisional application Ser. No. 60/395,382, filed Jul. 11, 2002. The disclosures of each of these applications is incorporated herein by reference in their entireties.

TECHNICAL FIELD

This invention relates generally to the field of cell biology of embryonic cells and neural progenitor cells. More specifically, this invention provides enriched populations of oligodendrocytes and their precursors, suitable for use in biological research, drug screening, and human therapy.

BACKGROUND

Oligodendrocytes play a vital physiological role in support of the central nervous system. Availability of oligodendrocytes for human therapy may facilitate healing of disabling conditions that result from defects in the myelin sheath that insulates nerve cells.

Multiple Sclerosis is a progressive and disabling demyelination disease, involving gradual destruction of the myelin sheath that surrounds the nerve cells in the brain and spinal cord. Symptoms range from numbness, visual impairment and cognitive changes, to paralysis. The disease is believed to have immunological and genetic components, often appearing in clinical form between ages 20 and 40. It affects about 300,000 people in the U.S. alone. Therapeutic modalities currently involve courses of β-interferon or corticosteroids. These drugs may shorten the symptomatic period during attacks, but generally do not prevent long-term disability.

Traumatic injury to the spinal cord causes demyelination of intact axons near the trauma site, which robs them of their capacity for neural transmission. There are about 11,000 new cases of spinal cord injury every year in the U.S. The SCI Information Network estimates that the lifetime direct costs to patients suffering from incomplete motor function at any level ranges from $400,000 to $2,200,000, not including lost wages and effects on the quality of life.

Myelin on cells of the central nervous system is put in place by oligodendrocytes, which wrap around axons in the vicinity, forming a myelin sheath. The role of oligodendrocytes and their progenitors in disease conditions is reviewed by Keirstead & Blakemore (Adv. Exp. Med. Biol. 468:183, 1999). Oligodendrocyte progenitors known as O-2A cells are present in normal adult CNS and in lesions of Multiple Sclerosis, and participate in remyelination (Scolding et al., Brain 121:2221, 1998; and Scolding et al., Neuroscience 89:1, 1999). Failure to remyelinate adequately may occur because oligodendrocytes proliferate symmetrically, using up the reservoir of progenitor cells where the damage is extensive.

Considerable research work has been done with a view to creating cell populations that could be used in regenerative medicine to restore neurological function (reviewed by Park et al., J. Neurotrauma 16:675, 1999). Keirstead et al. (J. Neuroscience 19:7529, 1999) isolated CNS precursors from the postnatal rat brain that generate oligodendrocytes and Schwann cells after transplantation. Svendsen et al. (J. Neurosci. Meth. 85:141, 1998) isolated precursor cells from the developing human cortex. Mujtaba et al. (Dev. Biol. 214:113, 1999) report isolation of neural precursors from embryonic stem cells.

PCT publication WO 97/07200 (Stanford U.) shows cultures of oligodendrocyte precursors isolated from adult rat brain. PCT publication WO 01/28342 (Washington U.) proposes certain methods for culturing nerve cells in pre-conditioned oligodendrocyte culture medium. U.S. Pat. No. 5,753,506 (Johe, CNS Stem Cell Technology) relates to a culture system for maintaining stem cells isolated from neural tissue that have the capacity to differentiate into neurons, astrocytes, and oligodendrocytes. U.S. Pat. No. 6,238,922 (StemCells Inc.) proposes dissociation of neural tissue into cells that have the capability of differentiating into neurons and glia. U.S. Pat. No. 6,235,527 (Rao et al., U. Utah) relates to populations of mammalian CNS glial-restricted precursor cells dissociated from mammalian neural tube tissue and selected based on the A2B5 cell surface marker.

U.S. Pat. No. 5,968,829 (Cytotherapeutics) claims culture medium containing CNS neural stem cells that have the capacity to produce neurons, astrocytes, and oligodendrocytes. PCT publication WO 97/32608 pertains to genetically engineered primary oligodendrocytes fro transplantation-mediated delivery in the CNS. U.S. Pat. No. 5,830,621 (Signal Pharmaceuticals) describes a human oligodendrocyte cell line deposited with the ATCC under Accession No. CRL 11881. The line is essentially free of the characteristic markers GFAP, GalC, O4, and A2B5.

Unfortunately, it is not yet clear whether progenitors isolated from neural tissue will have sufficient replicative capacity to produce the number of cells necessary for human clinical therapy.

An alternative source is pluripotent cells isolated from early embryonic tissue. Embryonic stem (ES) cells were first isolated from mouse embryos over 25 years ago (G. R. Martin, Proc. Natl. Acad. Sci. U.S.A. 78:7634, 1981). ES cells are believed to be capable of giving rise to progeny of virtually any tissue type of the same species.

Fraichard et al. (J. Cell Sci. 108:3181, 1995) report in vitro differentiation of mouse ES cells into glial cells and functional neurons. Mujtaba et al. (Dev. Biol. 214:113, 1999) report isolation of neural precursors from mouse ES cells. Li, Smith et al. (Cur. Biol. 8:971, 1998) report generation of neuronal precursors from mouse ES cells by lineage selection. Brustle, McKay et al. (Proc. Natl. Acad. Sci. USA 94:14809, 1997; Science 285:754, 1999) report glial precursors derived from mouse ES cells as a potential source of myelinating transplants. McDonald et al. (Nat. Med. 5:1410, 1999; Proc. Natl. Acad. Sci. USA 97:6126, 2000) report that mouse ES cells form oligodendrocytes and myelinate in culture and after spinal cord transplantation. Human ES cells were not isolated until much more recently (Thomson et al., Science 282:114, 1998). Human ES cells require very different conditions to keep them in an undifferentiated state, or direct them along particular differentiation pathways (U.S. Pat. Nos. 6,090,622 & 6,200,806; PCT publications WO 99/20741 & WO 01/51616). For this reason, much less is known about how to prepare relatively homogeneous populations of differentiated cells from human ES cells.

PCT publication WO 01/88104 (Carpenter, Geron Corporation) describes neural progenitor cell populations obtained by differentiating human ES cells. Populations have been obtained that are over 90% NCAM positive, 35% β-tubulin positive, and 75% A2B5 positive. Zhang et al. (Nature Biotech. 19:1129, 2001) report differentiation of transplantable neural precursors from human ES cells. International Patent Application PCT/US02/19477 (Carpenter et al., Geron Corporation) describes ES cell derived neural cell populations in which at least 10% of the MAP-2 positive cells in the produced population express tyrosine hydroxylase, a marker for dopaminergic neurons.

Recently, Billon et al. (J. Cell Sci. 115:3657, 2002) describe the timing of oligodendrocyte development from genetically engineered mouse ES cells. Kuo et al. (Biol. Reprod. Dec. 11, 2002) report a population of monkey ES derived cells that were 28% GFAP positive; and Xian et al. (Stem Cells 21:41, 2003) report generation of oligodendrocytes from mouse ES cells using the lineage-specific transcription factor Olig2.

In order to realize the full potential of pPS cells in the management of human health and disease, it is necessary to develop new paradigms to generate enriched populations of cells useful for treating demyelination conditions.

SUMMARY

This invention provides a system for efficient production of primate cells of the glial lineage for use in research or the preparation of pharmaceutical compositions.

The differentiated cell populations of this invention are isolated or cultured in vitro, and are highly enriched for characteristics of glial cells, or cells capable of myelinating neural tissue. The cells can have morphological features of oligodendrocytes, expression of certain antibody-detectable or amplifiable markers listed later in this disclosure, or the ability to form oligodendrocytes upon further differentiation. The cells can also have certain functional features of oligodendrocytes, such as the ability to myelinate ganglia in a coculture assay, the ability to restore myelin to demyelinated axons in vivo, or the ability to improve neurological function in humans or non-human animals. One, two, three, or more of these features may be present in any combination.

The cell populations can be prepared from less differentiated stem cells of various kinds. Potential originating cells include primate pluripotent stem (pPS) cells derived from blastocysts (exemplified by embryonic stem cells) or the germinal tissue of early embryos. Accordingly, the cells will have the characteristic of being the progeny of the tissue from which they originated, which can be confirmed by showing that the originating cells and the differentiated cells have the same genome.

Other aspects of the invention relate to methods for generating or maintaining the differentiated cells already described. The methods involve culturing multipotential or pluripotential stem cells in the presence of one or more growth or differentiation factors, such as those illustrated later in the disclosure.

By way of example, stem cells can be cultured in a medium containing one or more differentiation factors such as triiodothyronine (T3), selenium, or retinoic acid, with or without a mitogen such as fibroblast growth factor (FGF). Initial formation of the differentiated cells can occur in suspension culture, where oligodendrocyte lineage cells may form relatively homogeneous spheres. Other cell types can be removed by a suitable separation means, such as plating the culture onto a surface that selectively adheres the desired cell type. Optionally, the differentiated cells can be caused to proliferate further before or after selection by culturing with a mitogen such as FGF or epidermal growth factor, often in the presence of one or more differentiation factors, such as those used in the original derivation of the cells. Subsequently, the cells can optionally be caused to maturate further by culturing in the absence of mitogens, or in the presence of a surface such as poly-L-lysine that enhances late-stage differentiation.

The cells of this invention can be used for a number of commercially important applications. For example, the cells are suitable for screening compounds for an effect on glial cells, in which the presence of the compound is correlated with cell maintenance, toxicity, further differentiation, or the ability to function as a glial cell. The cells are also suitable for causing myelination of neighboring neurological tissue, both in vitro and in vivo.

The cells of this invention can also be used in the preparation of pharmaceutical compositions for human or animal therapy. The compositions can then be used to treat conditions such as those associated with a defect in the myelination of axons, or spinal cord injury.

Further aspects of the invention will be apparent from the description that follows.

DRAWINGS

Figure 4:
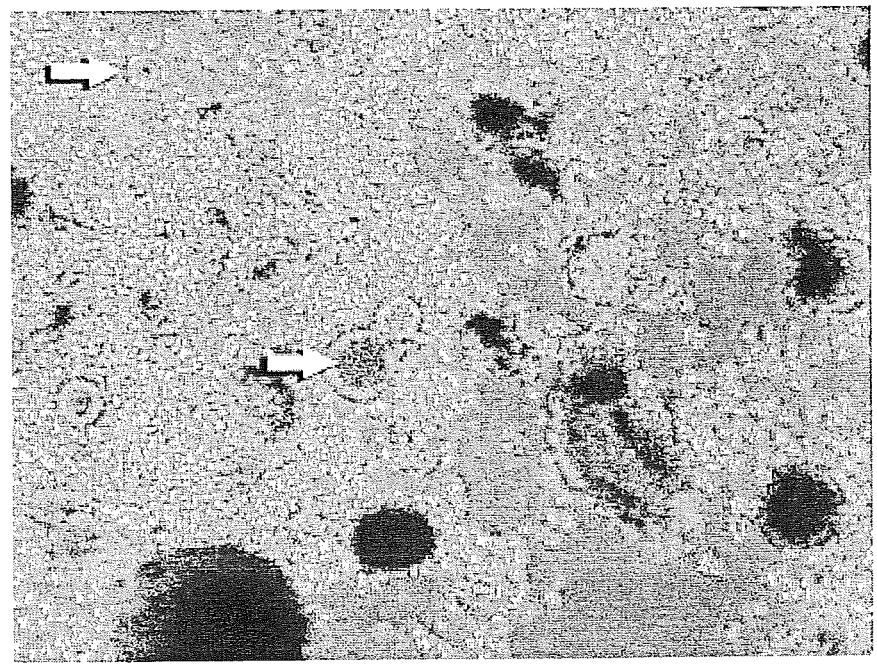

FIG. 4 shows the changes appearing after FGF was removed. The large aggregates dissociated, and the entire culture medium was flooded with single cells and small clusters. At the same time, new bright yellow spheres were observed (arrows).

Figure 5:
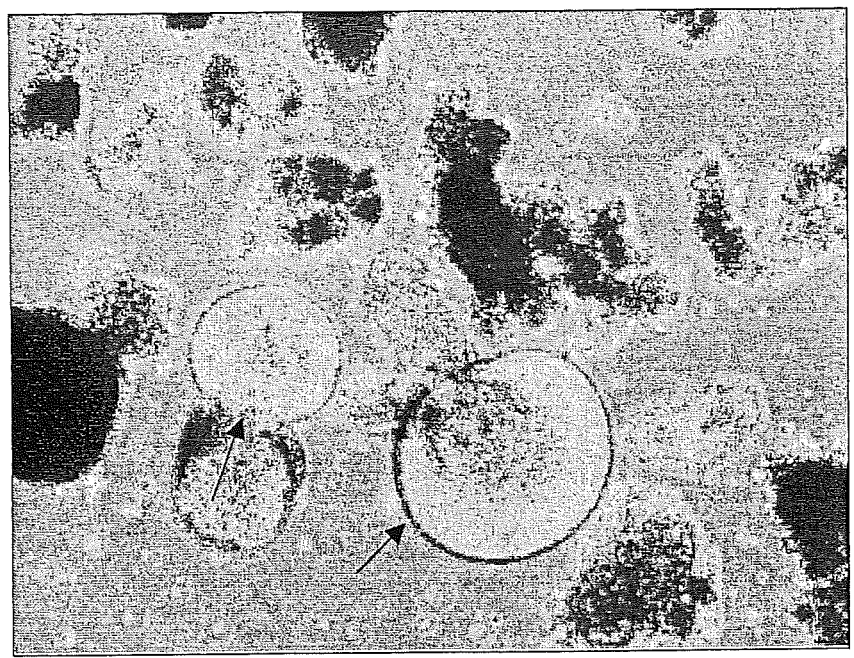
Figure 5:
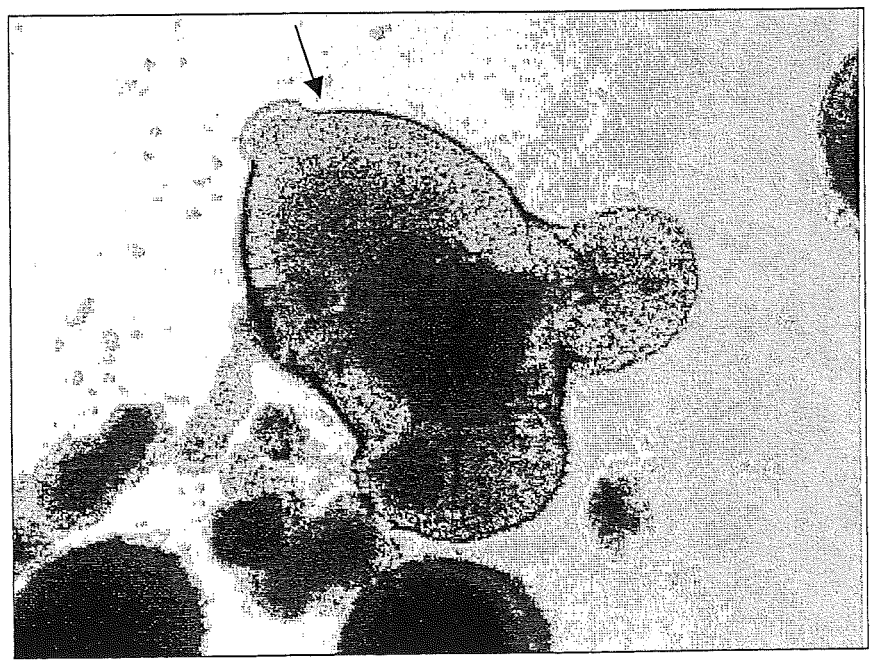

FIG. 5 shows bright-yellow spheres (arrows) growing as cells were cultured with epidermal growth factor, in the absence of FGF.

Figure 6:
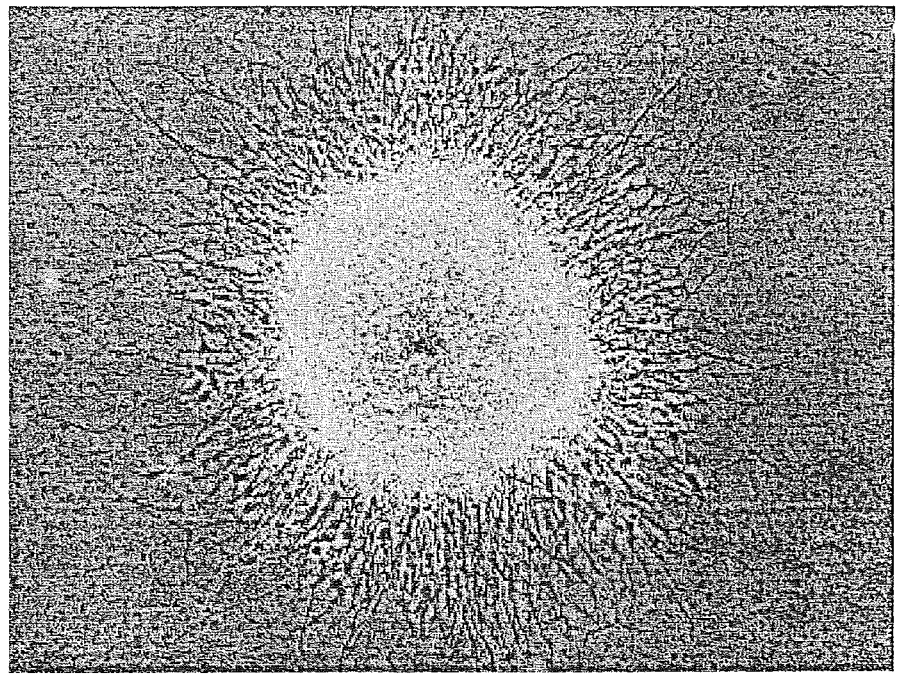
Figure 6:
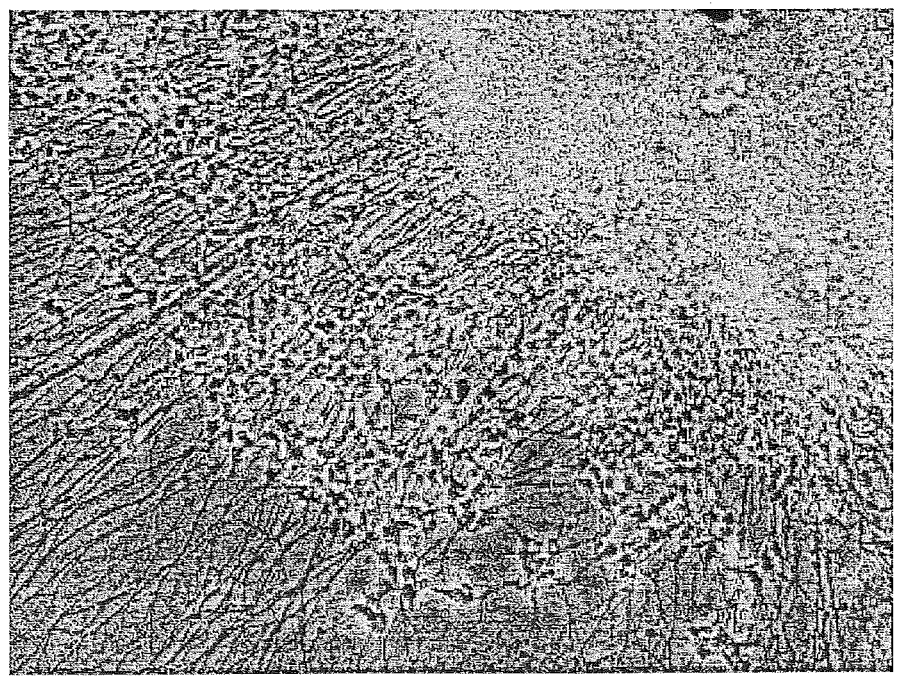

FIG. 6 shows migration and branching of the glial committed neural precursors from the spheres 2 or 3 days after plating on Matrigel®.

Figure 7:
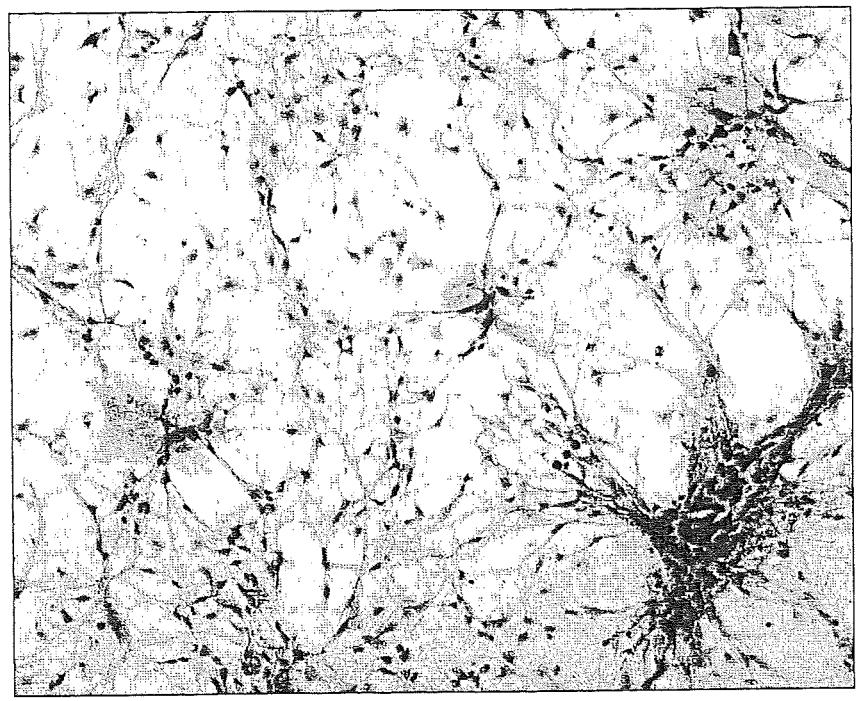
Figure 7:
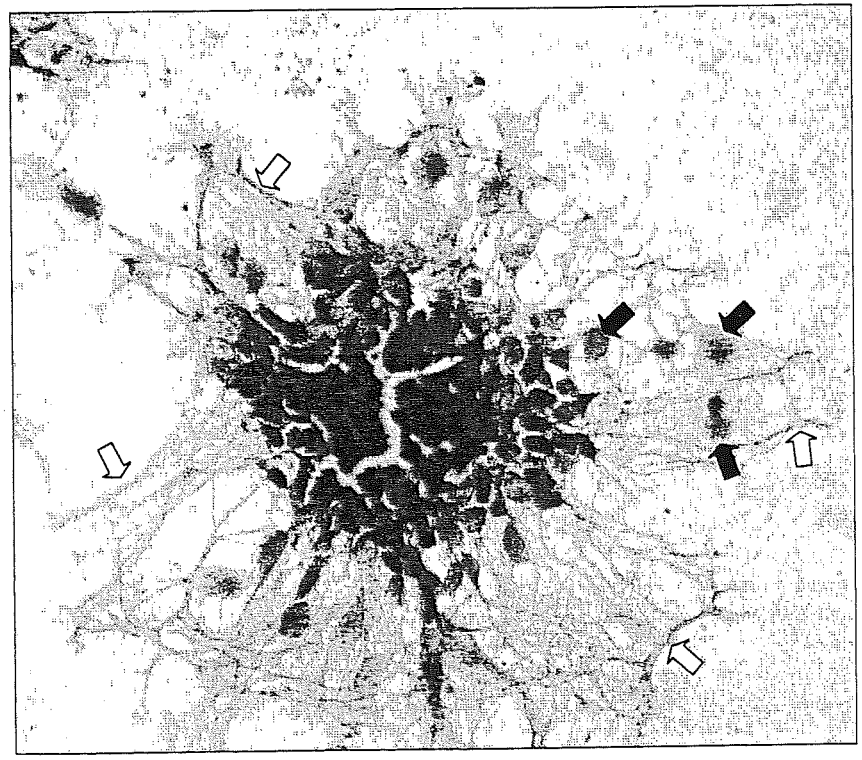

FIG. 7 shows the results in which oligodendrocyte lineage cells were selected by adherence onto Matrigel® for just 10-20 hours. Non-adherent cells were discarded, which eliminates virtually all of the cells not bearing oligodendrocyte markers. The adherent cells were then resuspended and expanded for 7 days in the presence of FGF, EGF, and glial precursor medium. This has the advantage of producing a more disperse cell population more suited for therapeutic administration and other purposes. The cells were then matured on poly-L-lysine laminin in the absence of mitogens. This micrograph shows staining for galactocerebroside (GalC; open arrows), with cell nuclei counterstained using hematoxin (closed arrows). The percentage of cells staining for GalC under these conditions was at least ~95%.

Figure 8:
Figure 8:
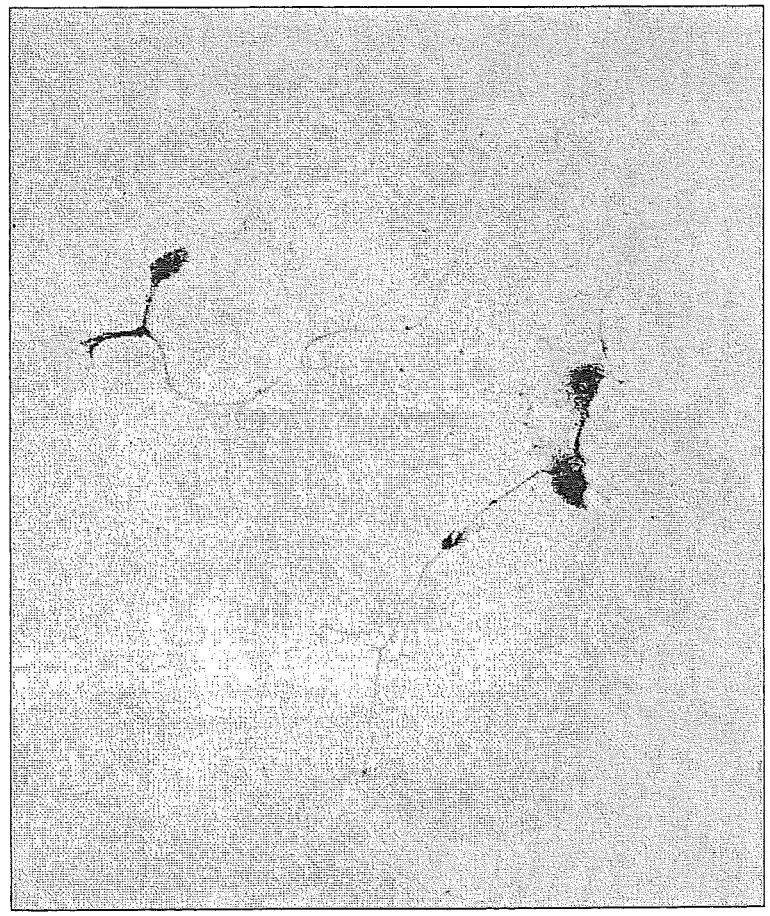

FIG. 8 shows a higher magnification of ES-derived oligodendrocytes. The cells have morphological features that are characteristic of mature oligodendrocytes: numerous complex processes that appear to have myelin webbing in between.

Figure 9:
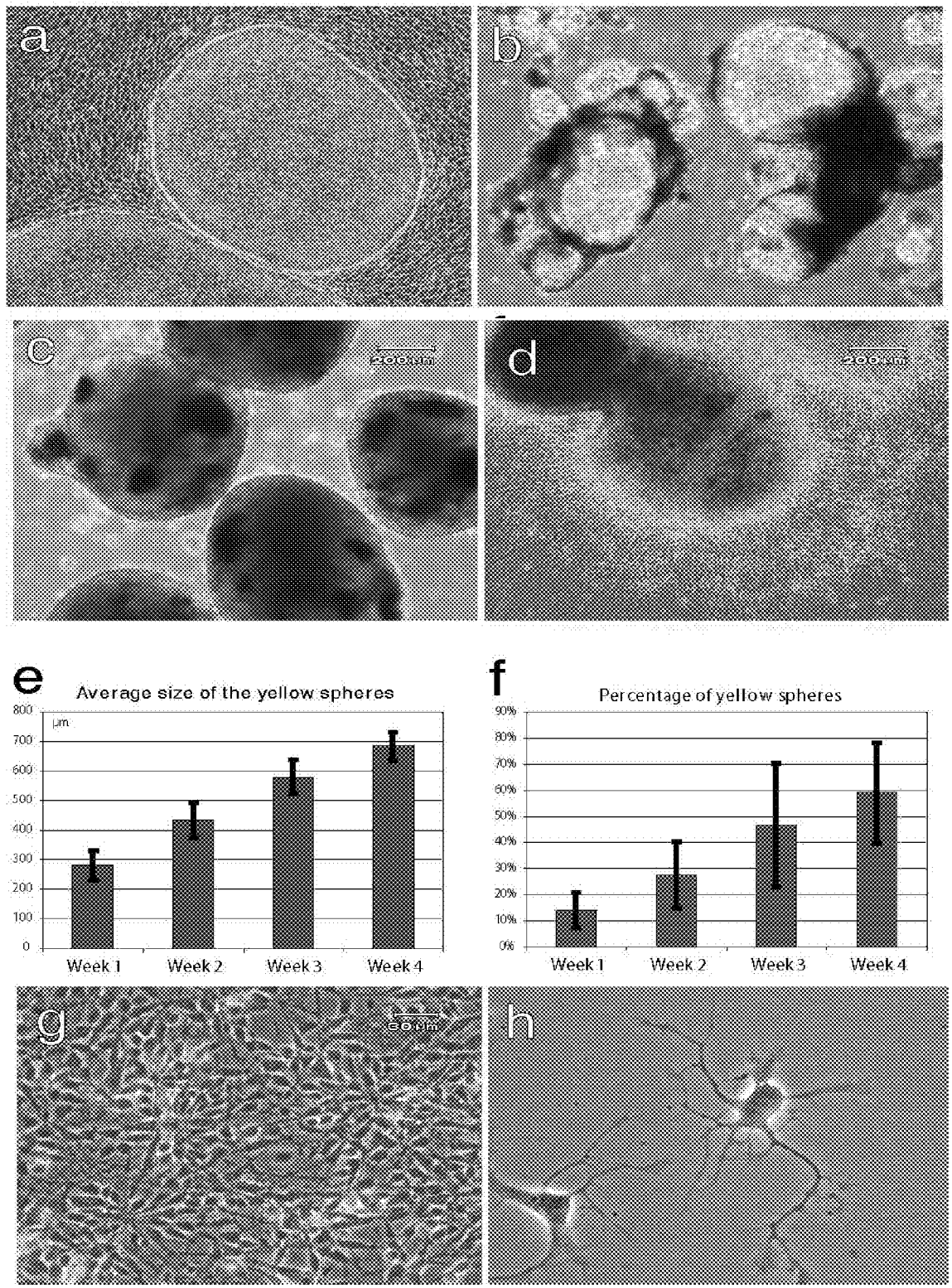

FIG. 9 shows the progression of cell morphology during differentiation. (A): Undifferentiated hES cells. (B): Transparent spheres growing from embryoid bodies in suspension cultures containing retinoic acid. (C): Expansion of yellow spheres containing oligodendrocyte precursors cells in the presence of EGF. (D) Oligodendrocyte lineage cells positively selected by plating onto Matrigel®. (E, F): Increasing prominence of oligodendrocyte precursors in the culture. (G, H): Subsequent plating causes further differentiation to mature oligodendrocytes.

Figure 10:
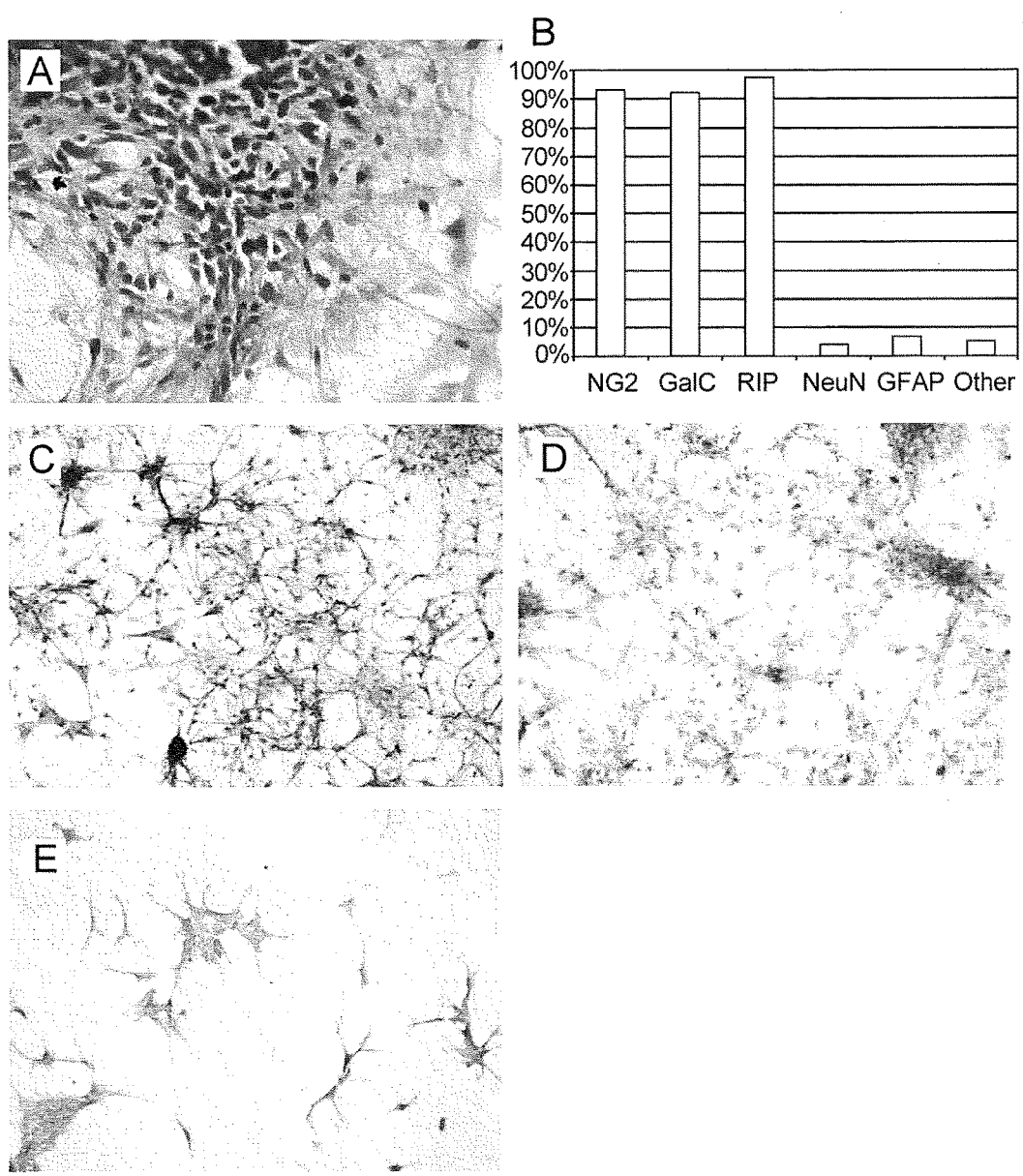

FIG. 10 shows an immunocytochemical analysis of the mature oligodendrocytes. One week after plating, the cells are positive for the early glial cell marker NG2 (A). Eight weeks after plating, the cells are positive for GalC (C), O4 (D), and RIP (E). Panel (B) shows number of cells staining with indicated markers.

Figure 11:
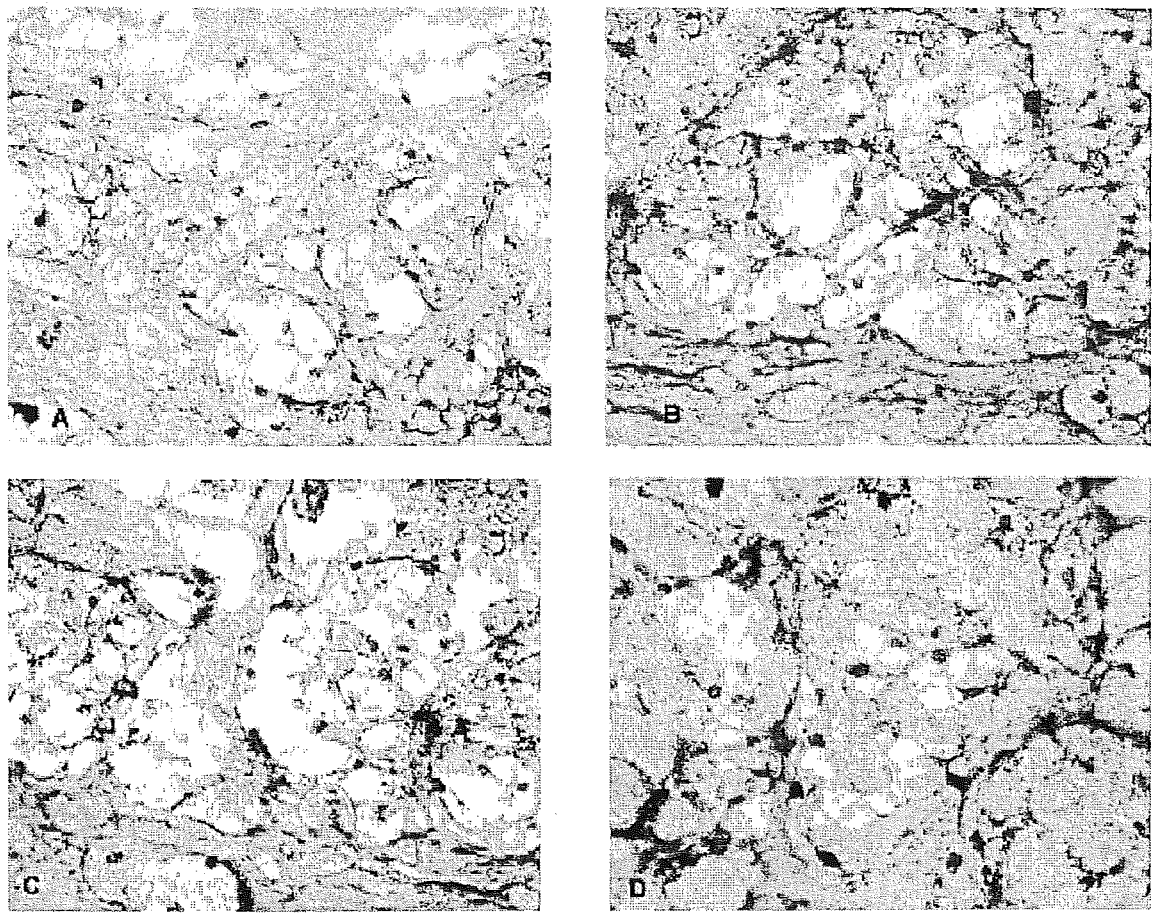

FIG. 11 shows tissue sections of oligodendrocyte precursors administered to the spinal cord of rats, stained with antibody specific for human nuclear protein.

Figure 12:
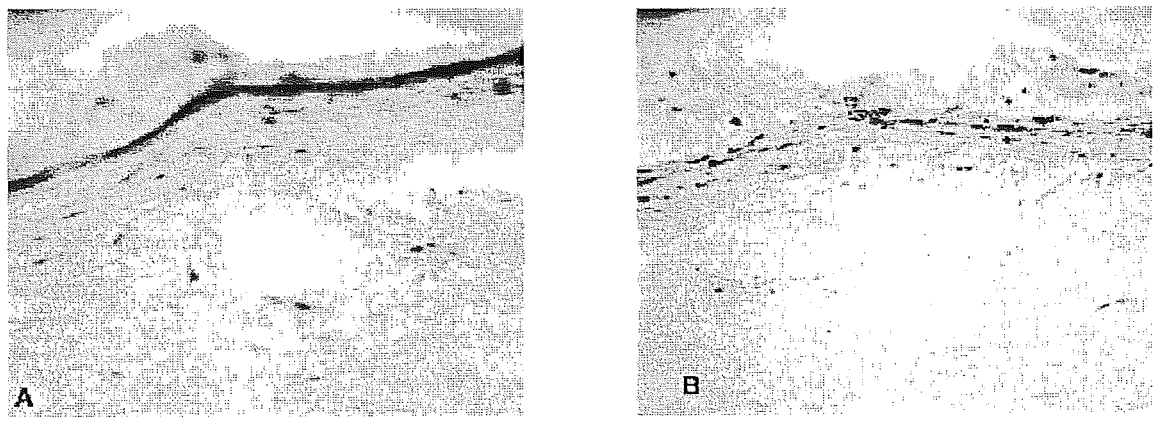

FIG. 12 shows that nine weeks after engraftment, the cells have migrated or proliferated into the white matter.

Figure 13:
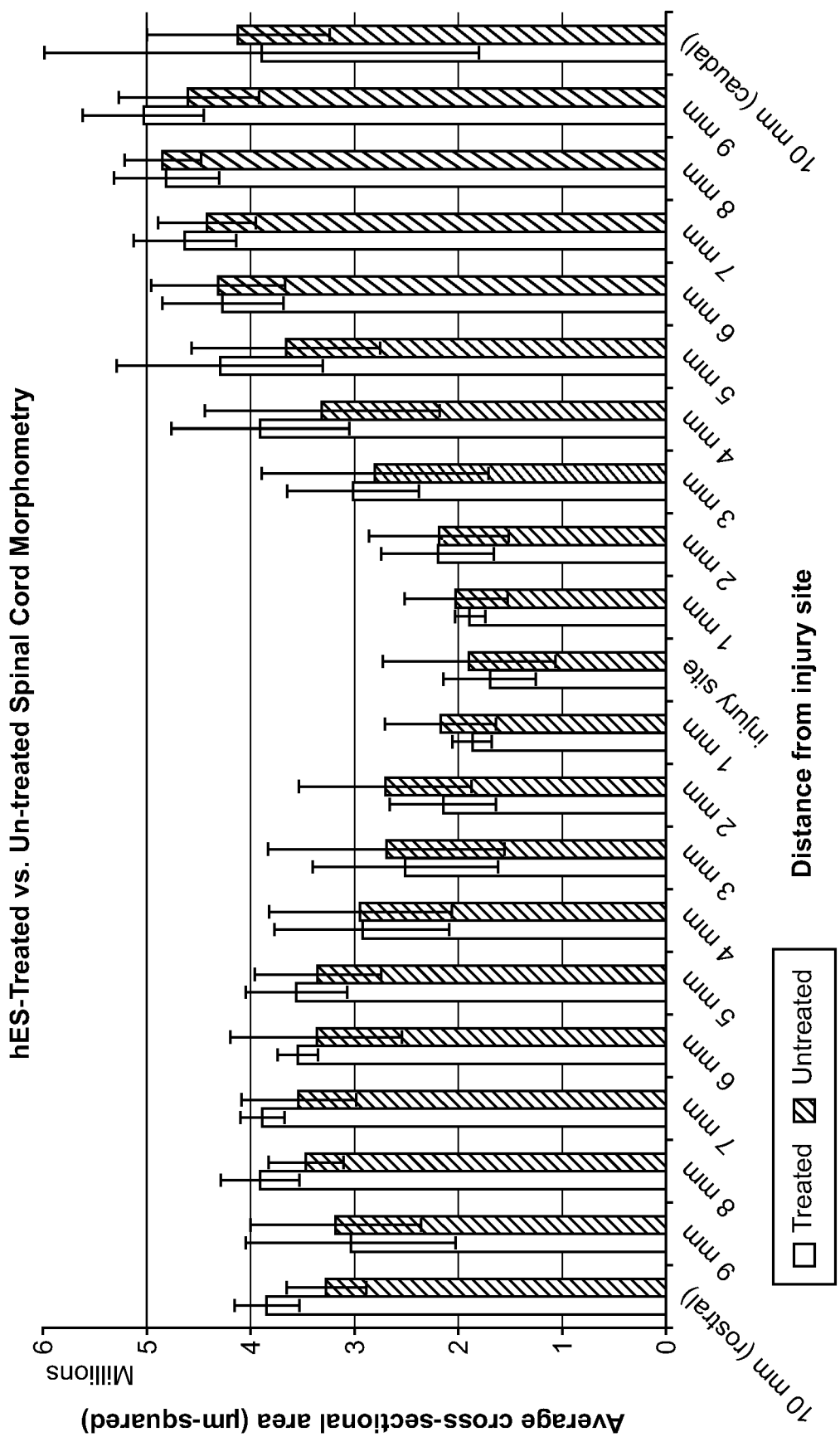

FIG. 13 shows the engrafted oligodendrocytes do not worsen the injury caused by secondary enlargement following contusion injury, measured as the cross-sectional area of the cord.

Figure 14:
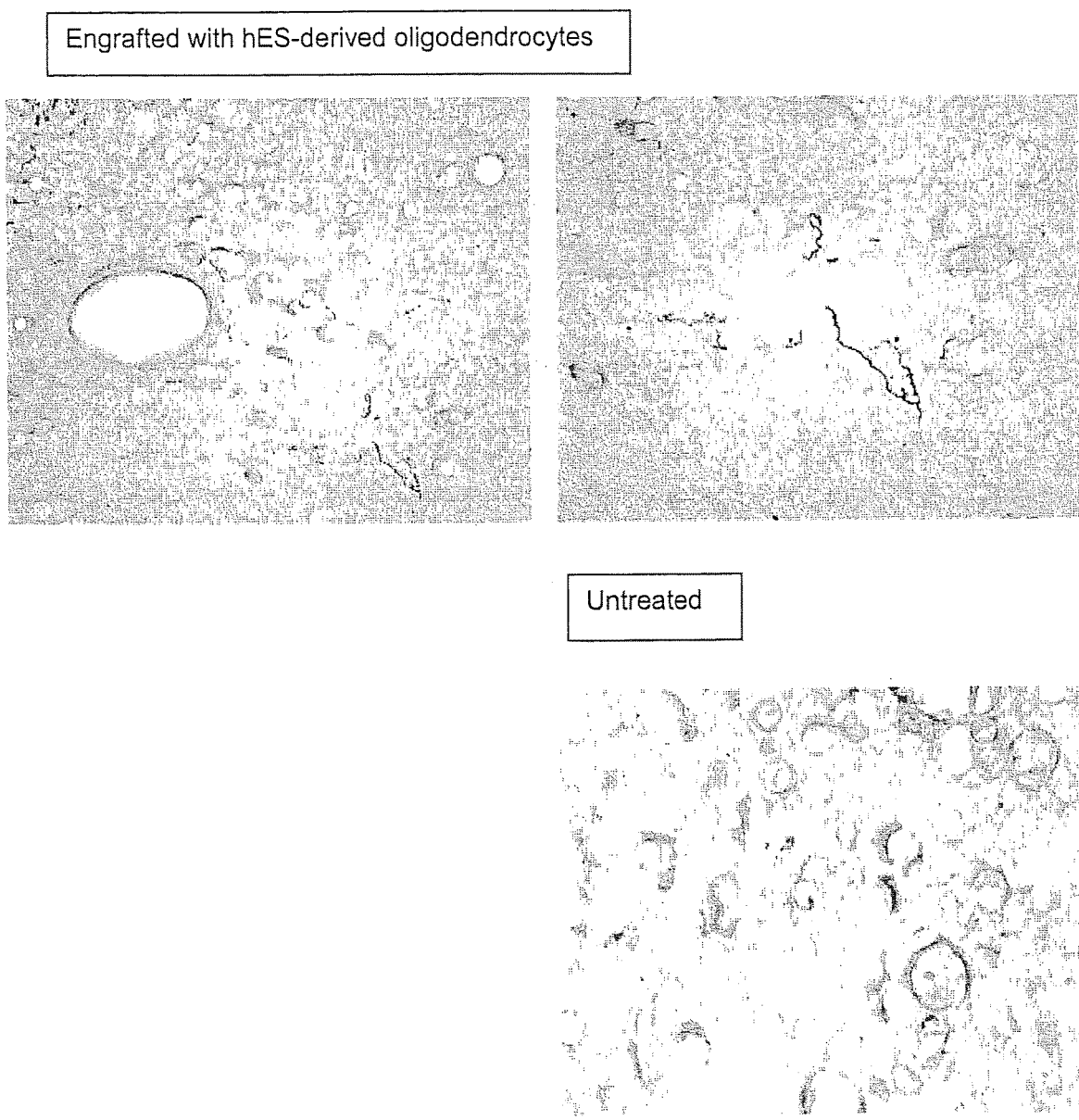

FIG. 14 shows that hES cells induce axonal branching. New axons are shown in the images from the oligodendrocyte engrafted animals (upper panels) as dark narrow lines of BDA staining. No branching was observed in untreated animals. The engrafted cells are inducing regenerative plasticity.

Figure 15:
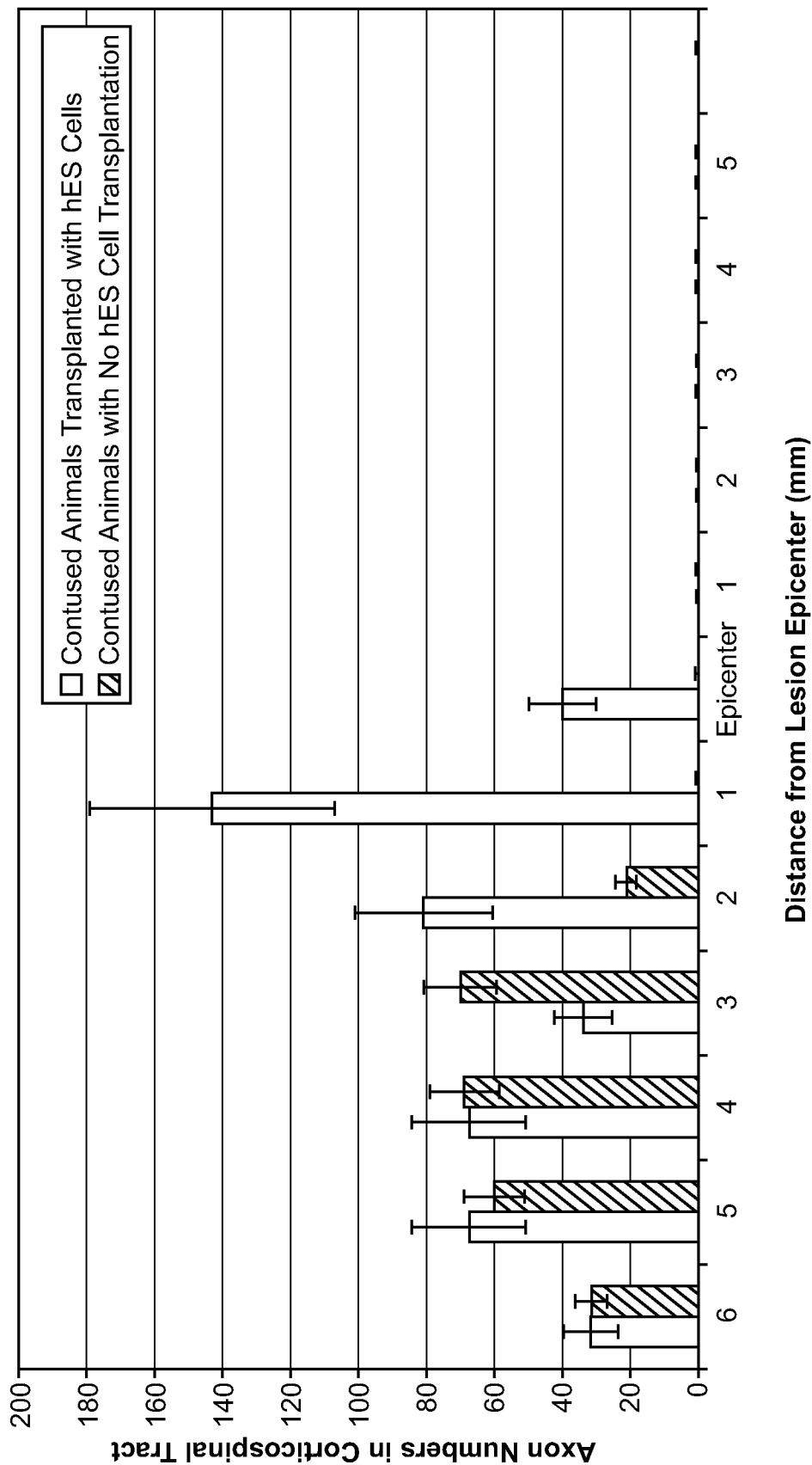

FIG. 15 shows quantitation of the neuronal branching from the site of injury (the epicenter) (mean±SEM for 3 sections per block). Treated animals had labeled axons at a significantly higher level right up to the epicenter on the rostral side of the injury.

Figure 16:
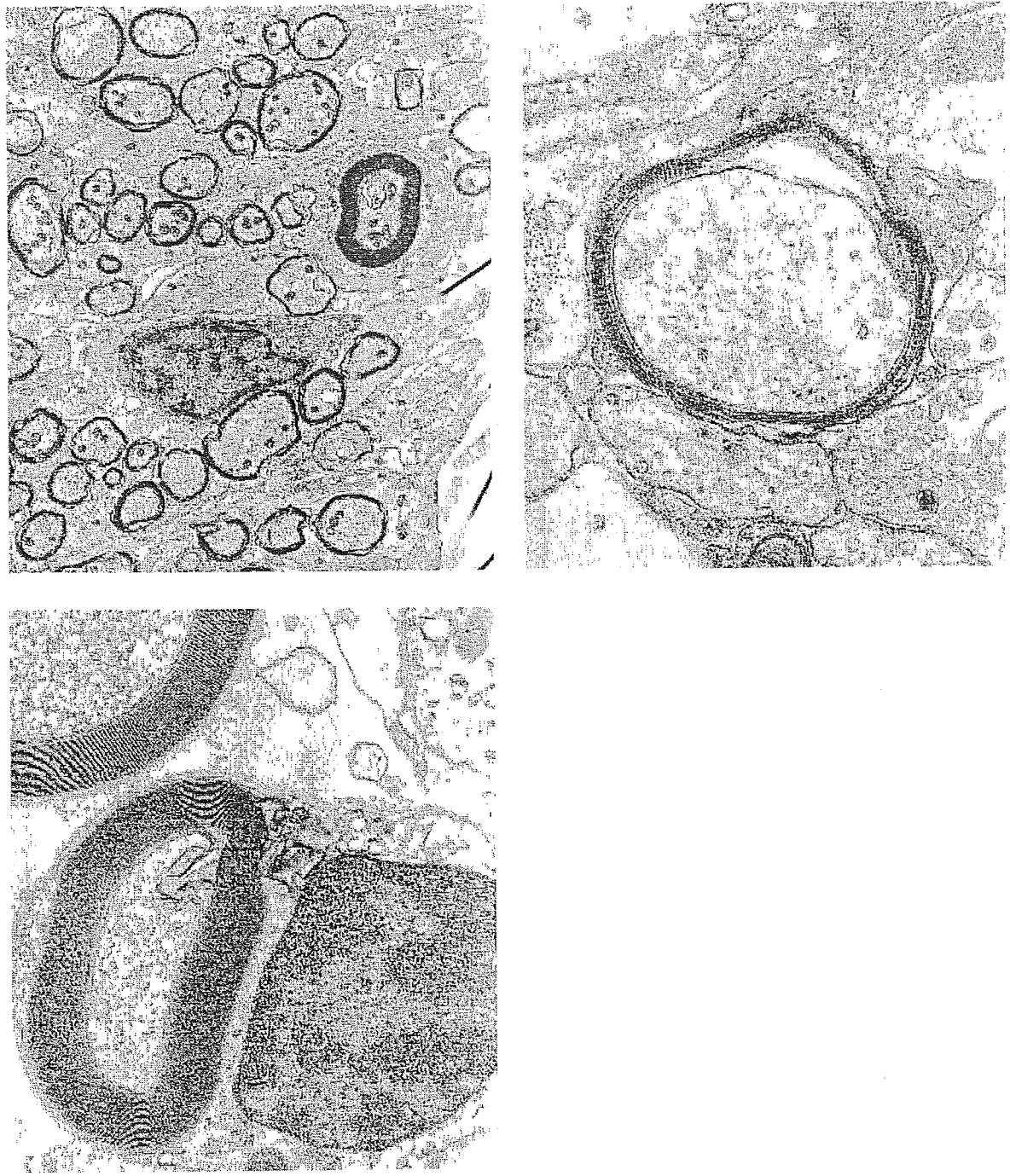

FIG. 16 shows evidence of substantial remyelination in the animals engrafted with hES derived oligodendrocytes. The thick circle in the upper electron micrograph is a normally myelinated fiber. The rest of the axons in the field show a thin layer of myelin. The axon in the upper right panel shows about 5 or 6 wraps, and evidence of ongoing remyelination. Only engrafted animals showed new myelin attributable to oligodendrocyte activity. This provides a mechanism to explain the behavioral improvement in the engrafted animals.

Figure 17:
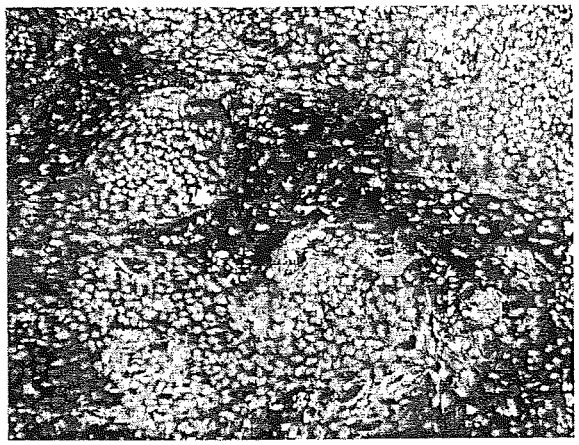
Figure 17:
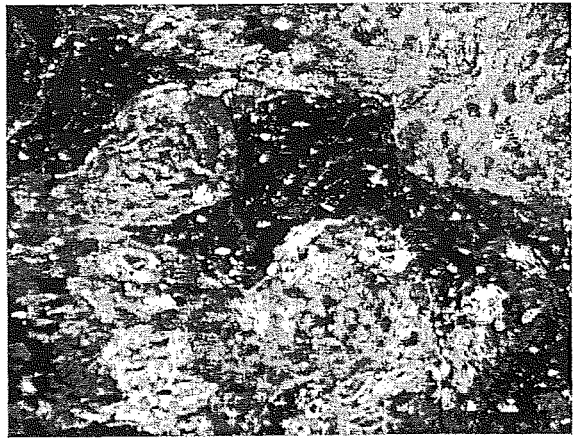
Figure 17:
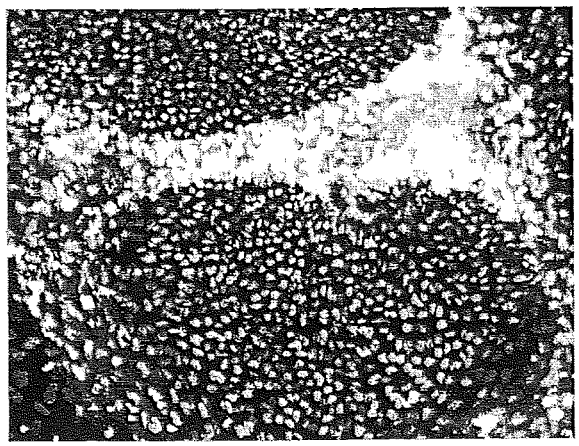
Figure 17:
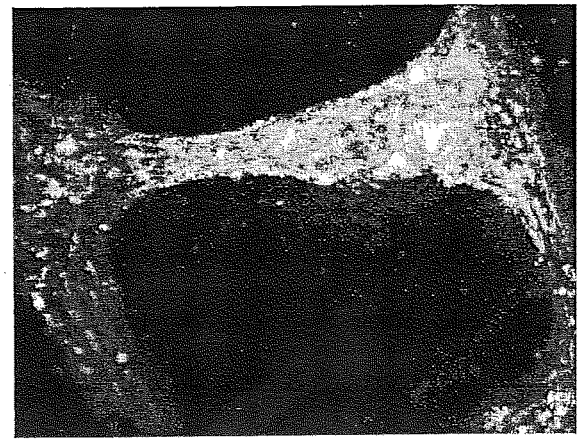

FIG. 17 shows markers detected on undifferentiated hES cell colonies (Left side: antibody plus DAPI; right side: antibody staining alone). Top row shows colonies labeled for SSEA-4, a marker of pluripotent cells. Bottom row shows stromal cells surrounding the colonies labeled for the mesodermal marker BMP4.

Figure 18:
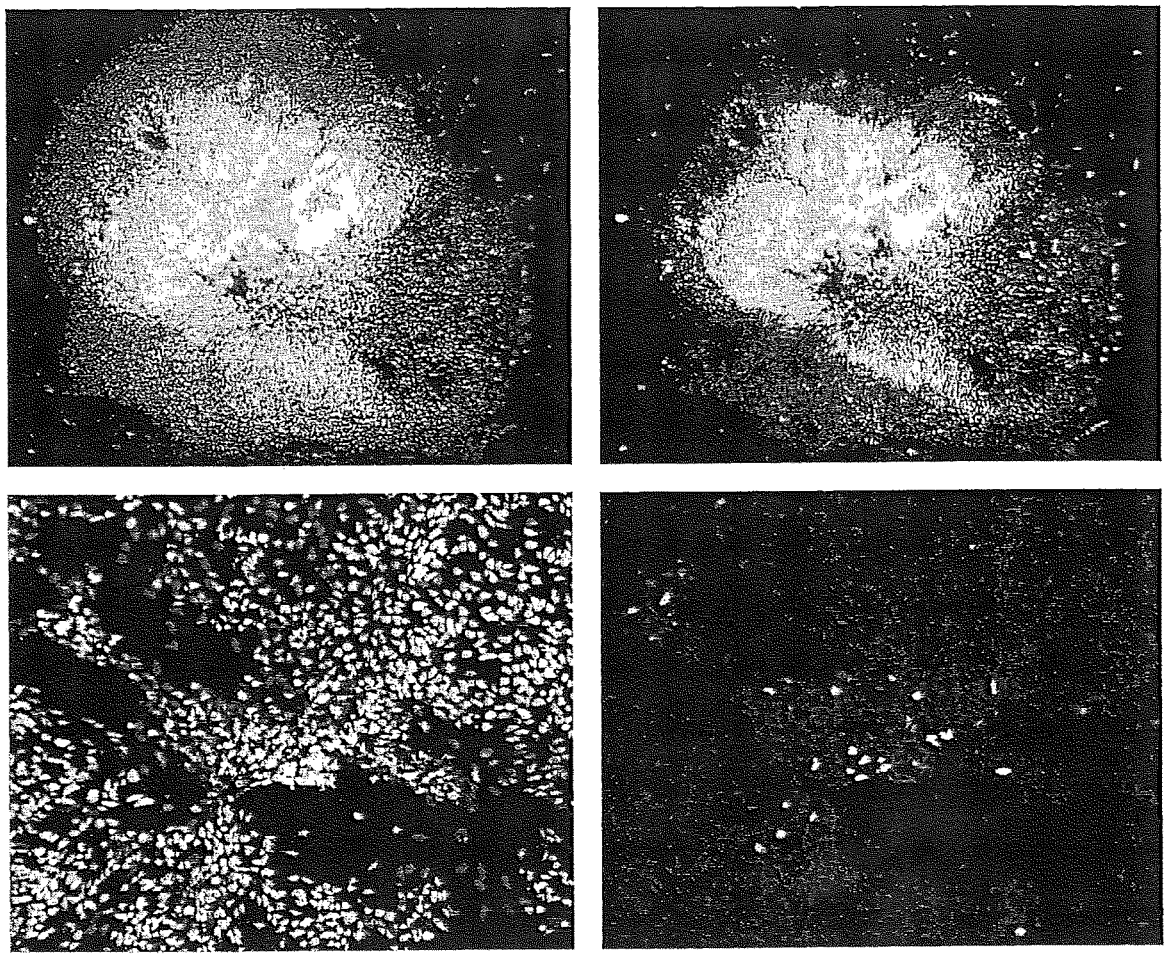

FIG. 18 shows the transient appearance of transcription factor Pax6 during differentiation. Top row shows staining towards the center of the cluster on day 10, already regulated down in the more differentiated cells towards the periphery. Bottom row shows virtually no staining at day 35 of differentiation.

Figure 19:
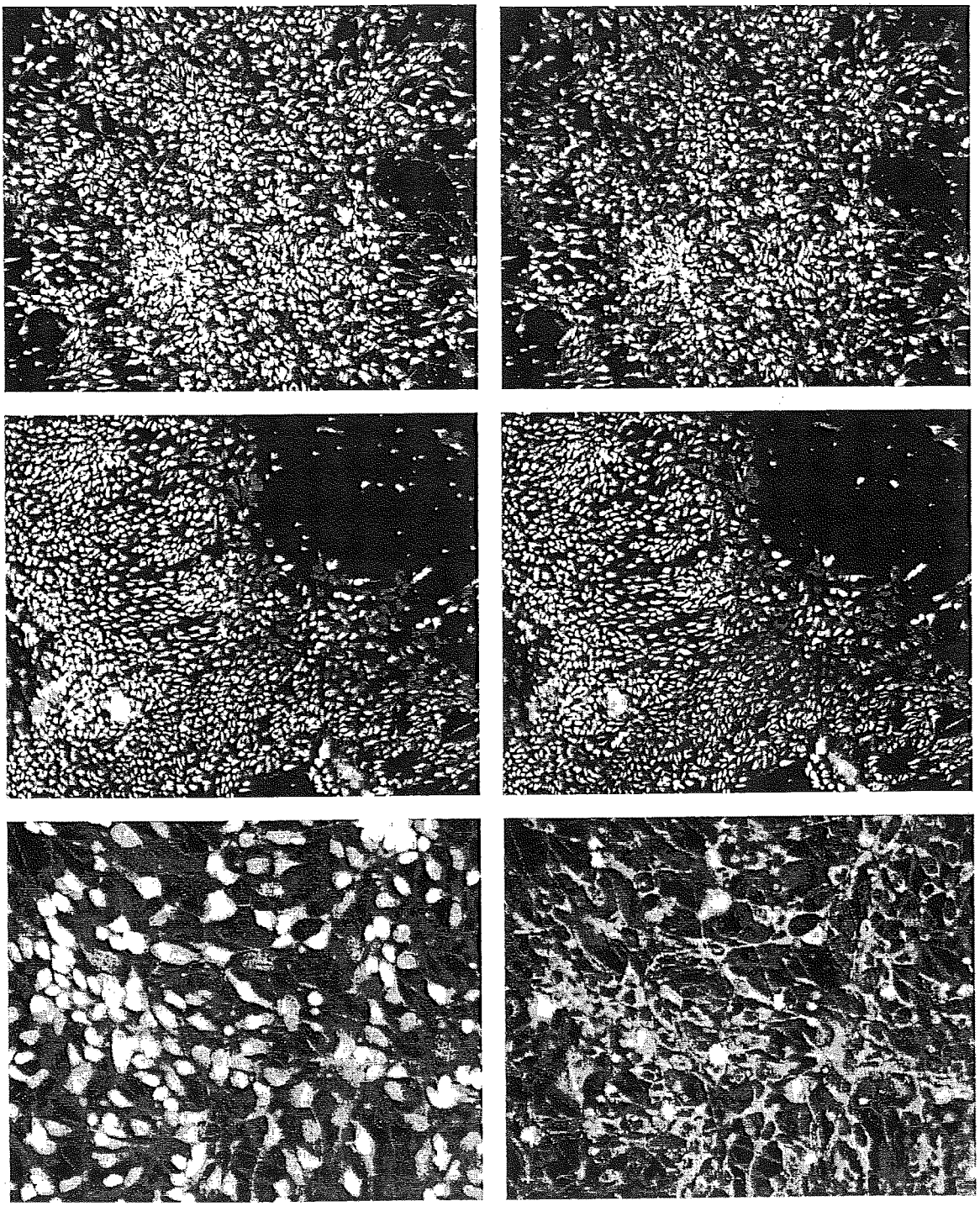

FIG. 19 shows markers detected in early-stage oligodendrocyte lineage cells, present at day 10 of differentiation. Top row: the transcription factor Olig1. Middle row: the transcription factor SOX10. Bottom row: oligodendrocyte progenitor marker A2B5.

Figure 20A:
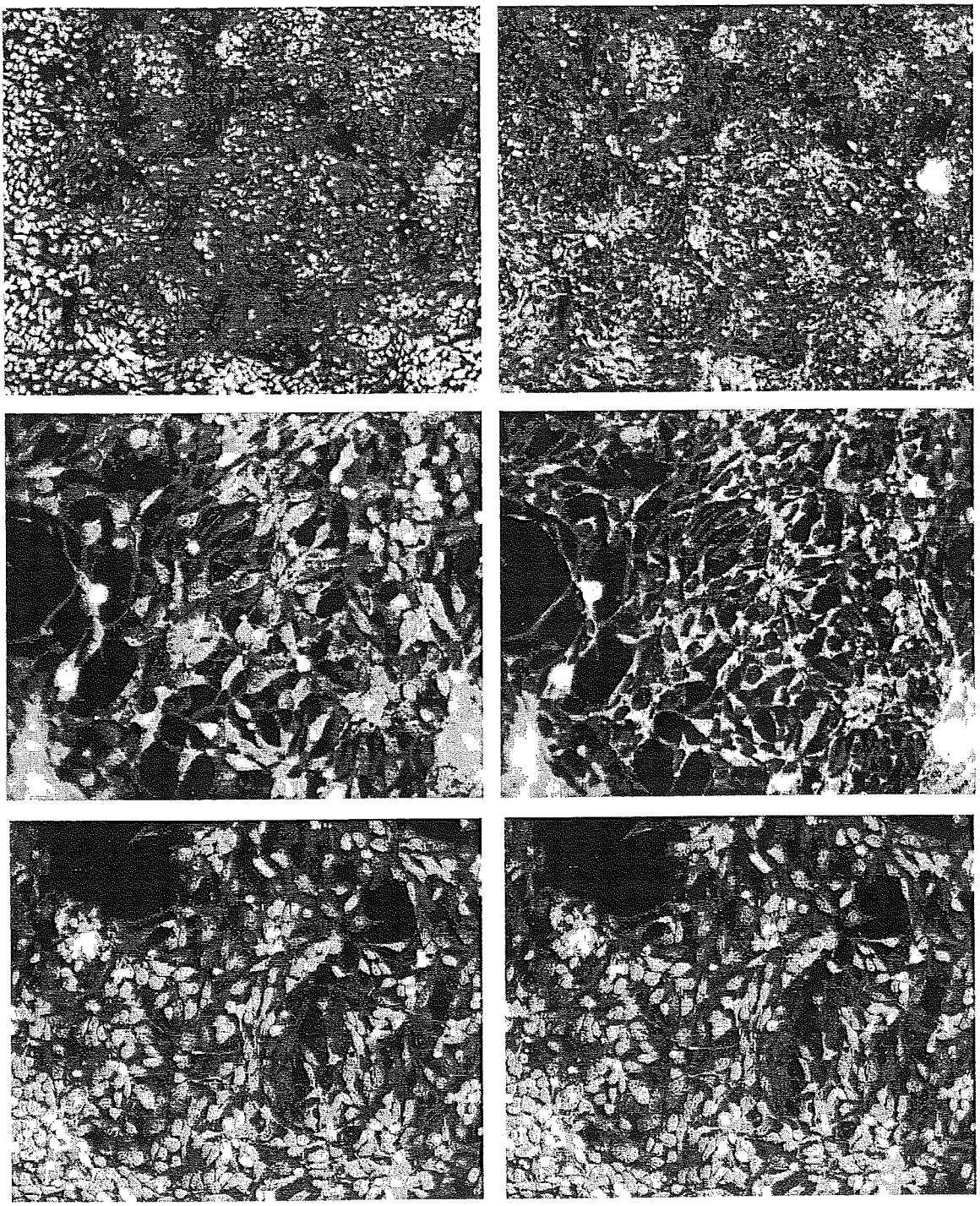
Figure 20B:
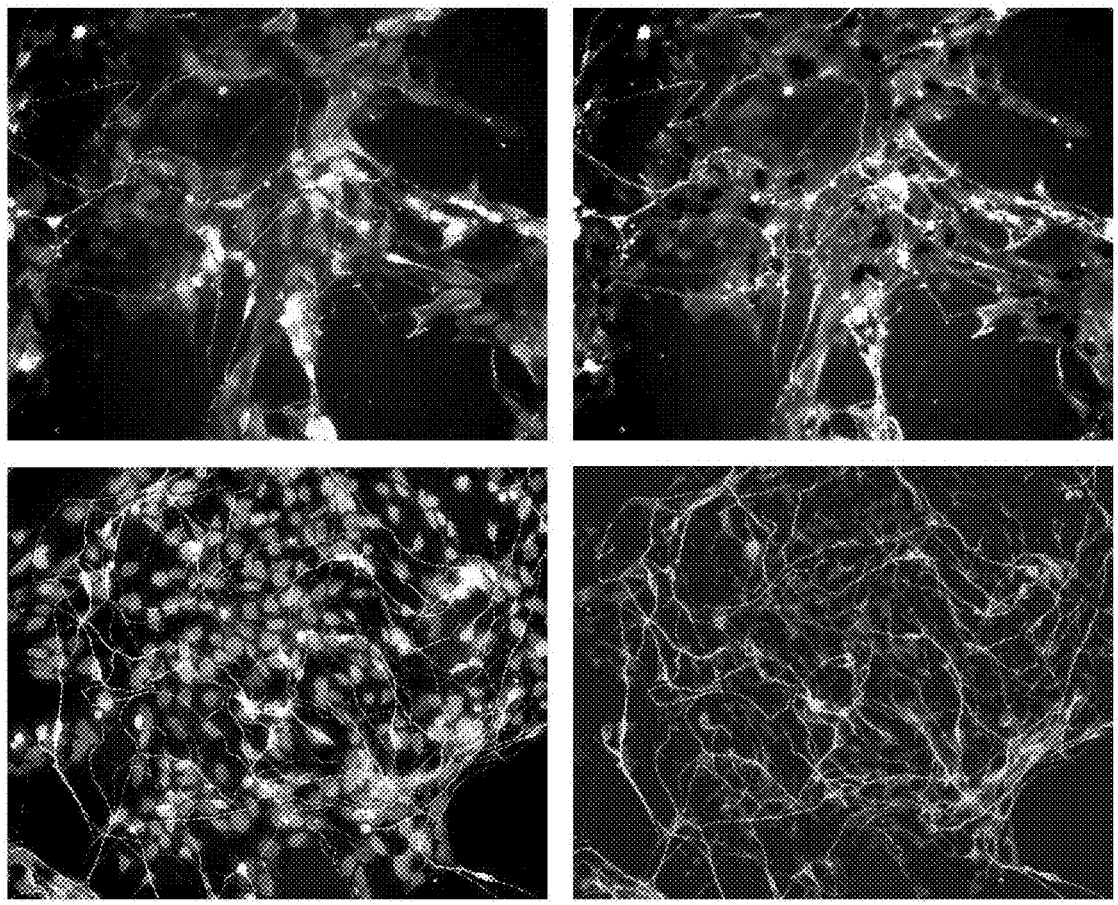
Figure 20B:
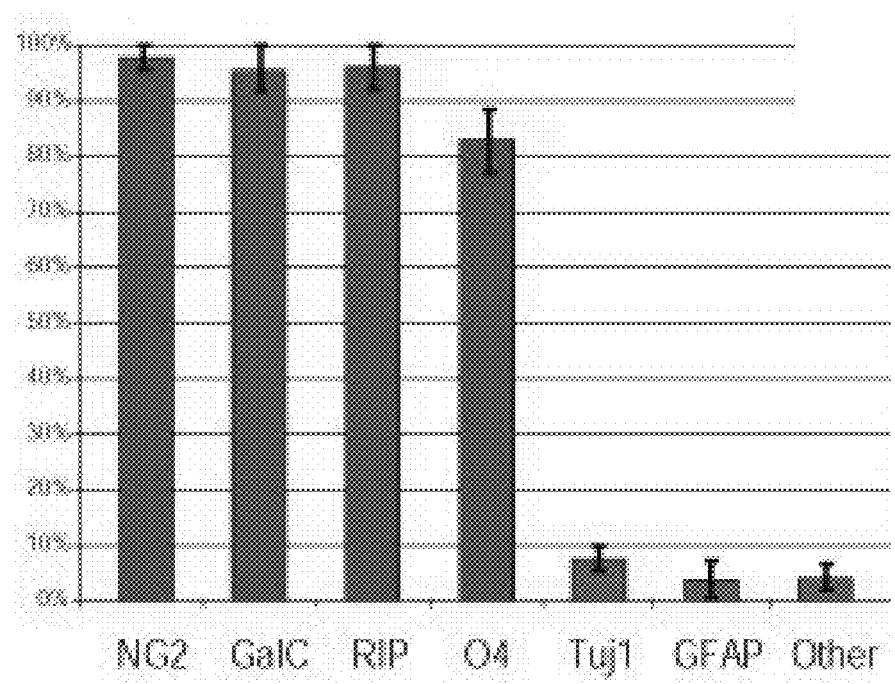

FIGS. 20A-20B show markers predominating in the oligoprogenitors suitable for transplant at day 35. First and second rows (20A): NG2 (chondroitin sulfate proteoglycan, a marker of oligodendrocyte precursors); Third row (20A): GalC; Fourth row (20B): O4; Fifth row (20B): Tuj1 (a marker of neurons). Virtually all of the cells bear oligodendroglial markers, but not markers for neuronal cells, mesenchymal cells, or undifferentiated hES cells (20B, bottom graph).

Figure 21:
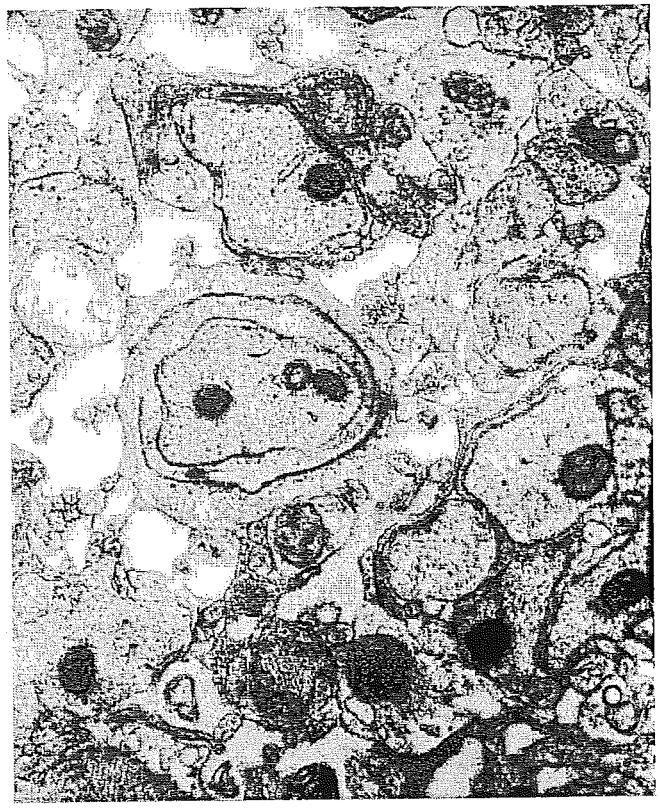
Figure 21:
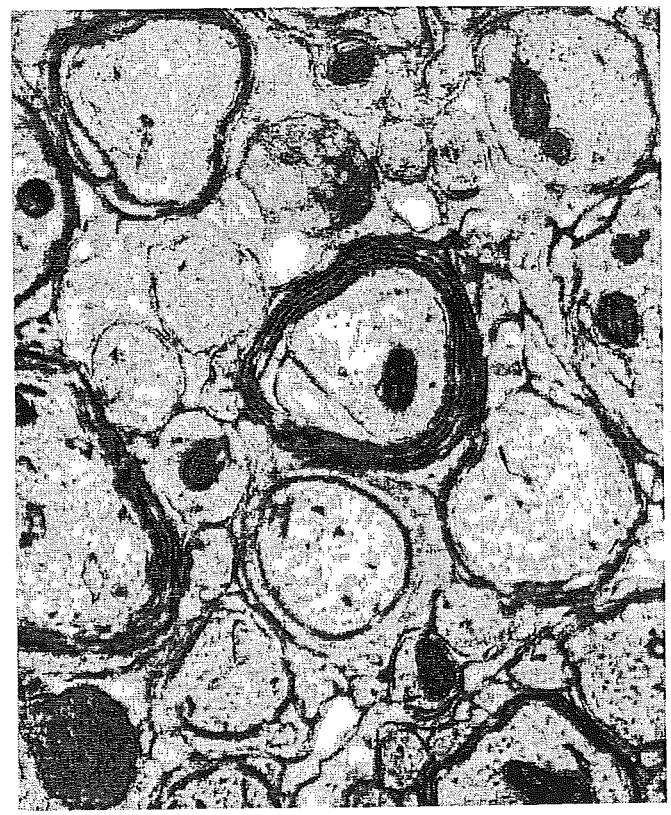

FIG. 21 shows the results of oligodendrocytes administered to Shiverer mice, which are genetically deficient in the ability to make myelin basic protein. Ultrastructurally, axons of shiverer mice are devoid of myelin or are surrounded by one or two uncompacted wraps of myelin (Upper Panel). Six weeks after transplantation of cells, electron microscopic analysis indicated multilayered compact myelin indicting the myelinogenic capability of the transplant population (Lower Panel). The compact myelin is being produced directly by the administered oligodendrocytes.

Figure 22:
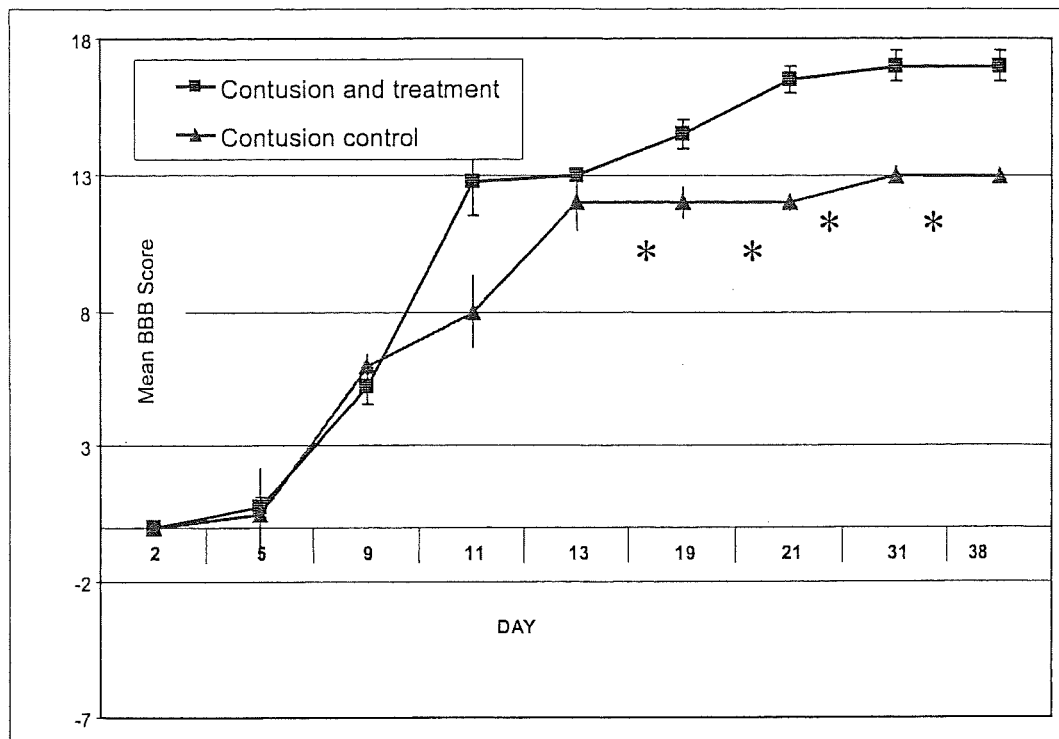
Figure 22:
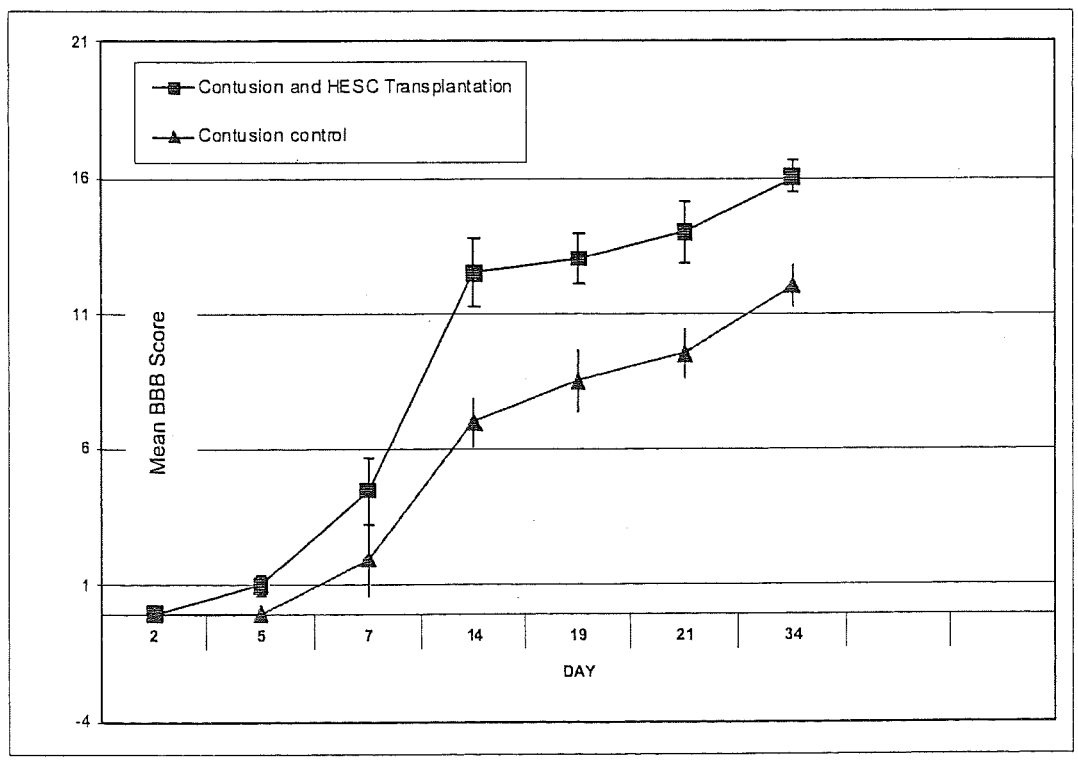

FIG. 22 shows the results of an experiment in which rats were contused in the spinal cord using an impactor, and then evaluated for spinal cord function in the ensuing period by quantitation on the BBB scale. Upper graph: 200 kiloDyne contusion; lower graph: 250 kiloDyne contusion. (■) animals treated with ES-derived oligodendrocytes 1 week after injury (n=5); (▲) control animals receiving the same contusion but no administered cells (n=3). Mean±SEM, for assessments done blinded. Animals engrafted with hES derived oligodendrocytes showed significantly better overground locomotion, persisting for more than 5 weeks after treatment.

DETAILED DESCRIPTION

This invention solves the problem of generating large populations of oligodendrocytes and their precursors by producing them efficiently from multipotent stem cells.

The differentiated cell populations are remarkably homogeneous. FIG. 7 shows an exemplary preparation of human cells with morphological features characteristic of oligodendrocytes. The population has been stained for GalC, a marker for cells of the oligodendrocyte lineage. FIG. 8 is a higher magnification view, showing the production of sheets of myelin poised to myelinate any neurons in the vicinity. The functional properties of these cells make them well suited for further characterization of the properties of oligodendrocytes, and for use in human therapy.

An ideal source of the cells of this invention is primate pluripotent stem (pPS) cells of various kinds. pPS cells can be coaxed into the oligodendrocyte pathway by selecting from amongst several suitable culture conditions and cofactors according to the strategy described below. It has been discovered that conversion of undifferentiated pPS cells into oligodendrocytes can be done at an efficiency of as much as 25% under optimized conditions.

The compositions and methods of this invention provide important advantages over previously available technology. Oligodendrocytes can be generated having any histocompatibility type, by differentiating them from pPS cells of the desired allotype. If desired, the cells can be genetically modified before or after differentiation in any way that enhances engraftment. Since the cells are derived from a natural cell line but do not require ongoing tissue dissection, they are ideal for meeting the quality control requirements for regulatory approval.

Importantly, there is an almost limitless supply of cells that can be produced from each starting stem cell population. As illustrated in Example 1, once oligodendrocyte lineage cells have been generated and selected, they can be expanded considerably by culturing in the presence of growth factors. Furthermore, the originating pPS cells can be caused to proliferate almost indefinitely, thereby providing a continual source for more differentiated cells.

The disclosure that follows provides further description of how to make and use the differentiated cells of this invention. The populations are remarkably uniform, and therefore suitable for use in a number of commercially important applications.

One aspect of the invention provides a differentiated cell population, in which at least about 80% of cells are progeny of primate pluripotent stem (pPS) cells; stain with antibody specific for NG2 proteoglycan (or other oligodendrocyte markers); and are negative for NeuN (or other markers of neuronal cells and other potential contaminants). The differentiated cell population may be part of a system of components suitable for generating oligodendrocyte lineage cells. The system may further comprise the line of pPS cells (such as human embryonic stem cells) from which the differentiated cells were produced. Optionally, at least 80% of the cells of the differentiated cell population also express A2B5 or PDGFRα. At least 20% of the cells may show a bipolar morphology characteristic of oligodendrocyte precursors.

Under some circumstances, the differentiated cell populations causes deposition of compact myelin around neuronal axons following implantation of the population into the spinal cord of a shiverer mutant mouse; or causes improvement in overground locomotion following implantation of the population in or around the spinal cord in a contusion-injured rat. Alternatively, the oligodendrocyte precursor cell populations of this invention may be further differentiated in vitro (for example, by culturing for 3 days on poly-L-lysine and laminin in the absence of mitogens). This may generate a more mature population in which at least 10% of the cells have complex processes characteristic of mature oligodendrocytes; and about 80%, 90%, 95% or more have mature oligodendrocyte markers such as GalC. The oligodendrocyte lineage cells made during the proliferative phase can be characterized not only by the markers they are expressing in the progenitor phase, but also their capacity to generate enriched populations of mature cells or their capacity to perform desirable functions in vivo.

As illustrated below, some differentiated cell populations of this invention can be obtained by a process in which the undifferentiated pPS cells are cultured in a medium containing a mitogen and at least two oligodendrocyte differentiation factors. For example, the undifferentiated pPS cells may be cultured in suspension so as to form cell aggregates in the presence of basic fibroblast growth factor (FGF), triiodothyronine (T3), retinoic acid, and perhaps selenium Further explanation and illustration of the invention is provided in the sections that follow.

Definitions

Oligodendrocytes are neural cells of ectodermal origin, forming part of the adventitial structure (neuroglia) of the central nervous system. They have variable numbers of veil-like or sheet-like processes that wrap around individual axons to form the myelin sheath of the CNS. They can be identified by morphological, phenotypic, or functional criteria as explained later in this disclosure.

"Neural precursor cells" or "neuroepithelial stem cells" are cells that can generate progeny that are either neuronal cells (such as neuronal precursors or mature neurons) or glial cells. The term "glial cells" encompasses mature oligodendrocytes, astrocytes, and committed precursors for either or both of these cell types.

"Oligodendrocyte precursors" are neural cells that are committed to form progeny comprising mature oligodendrocytes and/or more precursor cells, in preference to neurons or non-neurological tissue. Unless otherwise specified, they may but do not necessarily have the capability of making other types of glial cells, such as astrocytes. Reference in this disclosure to "oligodendrocytes" or "oligodendrocyte lineage cells" refers to both oligodendrocyte precursors and mature cells, unless otherwise indicated.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells, such as the various types of precursors listed above. These in turn can be differentiated further to cells further down the pathway, or to an end-stage differentiated cell, such as mature oligodendrocytes.

A "differentiation agent", as used in this disclosure, refers to one of a collection of compounds that are used in culture systems of this invention to produce differentiated cells of the oligodendrocyte lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms.

Unless otherwise specified, reference to "selenium" in this disclosure refers to any oxidation form of Se, including selenite ($SeO_3^{2-}$), selenate ($SeO_4^{2-}$), or senenide ($Se^{2-}$) in solution with any counter-ion.

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. Included in the definition of pPS cells are embryonic cells of various types, exemplified by human embryonic stem (hES) cells, and human embryonic germ (hEG) cells. The pPS cells are preferably not derived from a malignant source. It is desirable (but not always necessary) that the cells be euploid. Depending on their source and method of culture, the pPS cells may or may not be totipotent, in the sense that they have the capacity of developing into all the different cell types of the human body.

pPS cell cultures are described as "undifferentiated" when a substantial proportion of stem cells and their derivatives in the population display morphological characteristics of undifferentiated cells, distinguishing them from differentiated cells of embryo or adult origin. It is understood that colonies of undifferentiated cells within the population will often be surrounded by neighboring cells that are differentiated.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of pPS cells.

The term "embryoid bodies" refers to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

In assessment of phenotypic markers on individual cells or cell populations, unless stated wise, the cell is said to be "positive" for the marker if it shows substantially higher staining using specific antibody in a secondary immunocytochemistry stain, compared with isotype control. Unless stated otherwise, the cell is said to be "negative" if the marker is not antibody detectable by this type of immunocytochemical analysis.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and Current Protocols in Molecular Biology (F. M. Ausubel et al. eds., Wiley & Sons). Cell biology, protein chemistry, and antibody techniques can be found in Current Protocols in Protein Science (J. E. Colligan et al. eds., Wiley & Sons); Current Protocols in Cell Biology (J. S. Bonifacino et al., Wiley & Sons) and Current protocols in Immunology (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Tissue culture supplies and reagents are available from commercial vendors such as Gibco/BRL, Nalgene-Nunc International, Sigma Chemical Co., and ICN Biomedicals.

Specialized reference books relevant to this disclosure include *Principles of Neuroscience*, 4$^{th}$ Edition, Kandel et al. eds., McGraw-Hill 2000; *CNS Regeneration: Basic Science and Clinical Advances*, M. H. Tuszynski & J. H. Kordower, eds., Academic Press, 1999; *The Neuron: Cell and Molecular Biology*, 3$^{rd}$ Edition, I. B. Levitan & L. K. Kaczmarek, Oxford U. Press, 2001; *Glial Cells: Their Role in Behaviour*, P. R. Laming et al. eds., Cambridge U. Press, 1998; *The Functional Roles of Glial Cells in Health and Disease*, Matsas & Tsacopoulos eds., Plenum Pub. Corp, 1999; *Glial Cell Development*, Jessen & Richardson eds., Oxford U. Press, 2001; and *Man of Steel*, Adrian Havill, 1996.

Sources of Stem Cells

This invention can be practiced using stem cells of various types. Particularly suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells, as described below. The techniques of this invention can also be implemented directly with primary embryonic or fetal tissue, deriving neural cells directly from primary embryonic cells without first establishing an undifferentiated cell line.

The illustrations provided in the Example section ensue from work done with human embryonic stem cells. However, except where otherwise specified, the invention can be practiced using stem cells of any vertebrate species. Included are pluripotent stem cells from humans; as well as non-human primates, and other non-human mammals.

Embryonic Stem Cells

Embryonic stem cells can be isolated from primate tissue (U.S. Pat. No. 5,843,780; Thomson et al., Proc. Natl. Acad. Sci. USA 92:7844, 1995). Human embryonic stem (hES) cells can be prepared from human blastomeres using techniques described by Thomson et al. (U.S. Pat. No. 6,200, 806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen).

In one method, the zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells as described in Shamblott et al., Proc. Natl. Acad. Sci. USA 95:13726, 1998 and U.S. Pat. No. 6,090,622.

Briefly, genital ridges taken after ~8-11 weeks are rinsed with isotonic buffer, then placed into 0.1 mL 0.05% trypsin/ 0.53 mM sodium EDTA solution (BRL) and cut into <1 mm³ chunks. After disaggregation, the cells are incubated 1 h or overnight at 37° C. in ~3.5 mL EG growth medium (DMEM containing D-glucose, $NaHCO_3$; 15% ES qualified fetal calf serum; 2 mM glutamine; 1 mM sodium pyruvate; 1000-2000 U/mL human recombinant leukemia inhibitory factor; 1-2 ng/ml human recombinant bFGF; and 10 μM forskolin (in 10% DMSO).

The cells are then resuspended in 1-3 mL of EG growth medium, and plated onto a feeder layer (e.g., STO cells, ATCC No. CRL 1503, inactivated with 5000 rad γ-irradiation). The first passage is done after 7-10 days, and then cultured with daily replacement of medium until cell morphology consistent with EG cells is observed, typically after 7-30 days or 1-4 passages.

Other Stem Cells

By no means does the practice of this invention require that a human embryo or blastocyst be disaggregated in order to produce the pPS or embryonic stem cells useful as the starting material for making oligodendrocytes. hES cells can be obtained from established lines obtainable from public depositories (for example, the WiCell Research Institute, Madison Wis. U.S.A., or the American Type Culture Collection, Manassas Va., U.S.A.). U.S. Patent Publication 2003-0113910 A1 reports pluripotent stem cells derived without the use of embryos or fetal tissue. It may also be possible to reprogram cord blood or other progenitor cells into pPS cells by using a factor that induces the pluripotent phenotype (Chambers et al., Cell 113:643, 2003; Mitsui et al., Cell 113:631, 2003). Under appropriate conditions, any cell that otherwise meets the definitions for pPS or hES cells can be used for the derivation of oligodendrocyte lineage cells according to this invention.

Some of the techniques provided in this disclosure can also be used to maintain or advance the differentiation of more committed cell types, such as ectoderm cells, and neural cells or neural precursors obtained from fetal or adult tissue. Methods of obtaining such cells are described, for example, in U.S. Pat. Nos. 5,852,832; 5,654,183; 5,849,553; and 5,968,829; and PCT publications WO 98/50526 and WO 99/01159.

Propagation of pPS Cells in an Undifferentiated State pPS cells can be propagated continuously in culture, using culture conditions that promote proliferation without promoting differentiation. Exemplary serum-containing ES medium is made with 80% DMEM (such as Knockout DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.).

The pPS cells can be expanded in the undifferentiated state only by culturing in an environment that inhibits differentiation. Traditionally, pPS cells are cultured on a layer of feeder cells derived from embryonic or fetal tissue of the mouse. Culture plates are plated with 375,000 irradiated mEFs per well, irradiated to inhibit proliferation but permit synthesis of factors that support pPS cells, and used 5 h to 4 days after plating (U.S. Pat. No. 6,200,806). Human feeder cells have recently been developed that support proliferation of human embryonic stem cells without differentiation (WO 01/51616; U.S. Ser. No. 09/888,309; Geron Corp.). The cells are obtained by differentiating hES cells, selecting cells that have the desired activity, and then immortalizing them by transfecting them to express telomerase reverse transcriptase.

pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells $cm^{-2}$ (optimally 90,000 $cm^{-2}$ to 170,000 $cm^{-2}$). Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or human feeder cells derived from pPS cells. Medium can be conditioned by plating the feeders at a density of ~5-6×$10^4$ $cm^{-2}$ in a serum free medium such as KO DMEM supplemented with 20% serum replacement and 4 to 8 ng/mL bFGF. Medium that has been conditioned for 1-2 days is supplemented with further bFGF, and used to support pPS cell culture for 1-2 days. Features of the feeder-free culture method are further discussed in International Patent Publications WO 99/20741 & WO 01/51616; and Xu et al., Nat. Biotechnol. 19:971, 2001.

Under the microscope, ES cells appear with high nuclear/cytoplasmic ratios, prominent nucleoli, and compact colony formation with cell junctions that are difficult to discern. Primate ES cells typically express stage-specific embryonic antigens (SSEA) 3 and 4, markers detectable using antibodies designated Tra-1-60 and Tra-1-81 (Thomson et al., Science 282:1145, 1998), and telomerase activity. Differentiation of pPS cells in vitro results in the loss of SSEA-4, Tra-1-60, and Tra-1-81 expression, and increased expression of SSEA-1, which is also found on undifferentiated hEG cells.

Making Oligodendrocytes from Stem Cells

Oligodendrocyte lineage cells of this invention are obtained by culturing stem cells in a special growth environment that enriches and expands cells with the desired phenotype. The growth environment may specifically direct differentiation into the oligodendrocyte lineage, promote outgrowth of the desired cells, inhibit growth of other cell types, or perform any combination of these activities.

This section is a guide that illustrates to the reader some approaches that can be taken to obtain oligodendrocytes of this invention. Except where otherwise required, explanations as to the underlying mechanism of the process are provided only as working hypotheses to assist in further elaboration. It is not necessary that the user understand the hypothesis, nor is it required that the invention conform to the hypothesis in order to be put into practice. Now the applicants have demonstrated that oligodendrocytes can be made from pluripotent stem cells, further adjustments to the protocols can be made, and alternative methods can be found to obtain the novel products described in this disclosure.

Steps to generate oligodendrocytes from pPS cells can include: a) obtaining a population of cells committed to make oligodendrocytes; b) expansion of oligodendrocyte lineage cells; and c) further maturation of cells to late-stage oligodendrocytes.

Directing Stem Cells into the Oligodendrocyte Lineage

The process of generating oligodendrocytes typically involves two aspects: causing the originating stem cell population to differentiate, and causing oligodendrocyte lineage cells to become the predominant cell type. These events can occur sequentially or concurrently.

The process of differentiation can be induced by causing the pPS cells to form embryoid bodies or aggregates: for example, by overgrowth of a donor pPS cell culture, or by culturing pPS cells in suspension in culture vessels having a substrate with low adhesion properties that allows embryoid bodies to form. In an exemplary method, confluent monolayer cultures of hES cells are harvested and then plated in non-adherent cell culture plates, keeping the cells in suspension, and providing regular feeding with nutrient medium.

Alternatively or in addition, the differentiation process can be initiated by culturing with certain factors that prevent the cells from maintaining the undifferentiated phenotype. The initial differentiation factors need not limit differentiation into the oligodendrocyte lineage, but should be inclusive of oligodendrocytes or their precursors within the range of cell types in the differentiated population. Exemplary growth factors of this type are ligands that bind retinoid receptors, or activate the extracellular-signal-regulated kinase (ERK) pathway. A mitogen such as a fibroblast growth factor (or those listed in the next section) is typically included in the culture medium to promote proliferation while the differentiation process is under way.

At some stage, the culture can be directed more specifically into the oligodendrocyte lineage. This can be done by including in the culture medium a factor that more specifically promotes the growth of oligodendrocytes. Exemplary oligodendrocyte differentiation factors are ligands and antibodies that bind thyroid hormone receptors on the cell surface or in the nucleus, exemplified by T3 (3,5,3'-triiodo-L-thyronine) and T4 (L-thyroxin) at about 40 ng/mL. Thyroid hormones are believed to increase expression of retinoic acid receptors, and otherwise promote differentiation into cells of the oligodendrocyte lineage.

Another oligodendrocyte differentiation factor is selenium, an antioxidant that is believed to participate in the upregulation of myelin genes in differentiating oligodendrocytes. Other candidate differentiation factors are other antioxidants like Vitamin E, and factors that increase activity of enzymes for which selenium is a cofactor, such as thioredoxin reductase and the family of iodothyronine deiodinases. Selenium is especially effective when included in the culture medium at relatively high concentrations of at least 20 ng/mL or 100 ng/mL, in the form of selenite ion ($SeO_3^{2-}$). Other candidate differentiation factors or cofactors include bone morphogenic protein (BMP), sonic hedgehog (SHH), and leukemia inhibiting factor (LIF). Also contemplated are combinations of oligodendrocyte differentiation factors produced by neural tissue, which can be generated by coculture with selected dissociated neural tissue or cell lines, exemplified by embryonic CD-1 mouse brain, and factor-containing extracts obtained from the tissue or cell line.

It has been discovered that oligodendrocytes can be generated in a surprisingly efficient manner by combining all of these techniques together: initiating differentiation by forming embryoid bodies in the presence of a mitogen, general differentiation factors like retinoic acid, and specific differentiation factors like thyroid hormone and sodium selenite. Non-limiting illustrations provided in the Example section include these factors and other standard culture ingredients, such as nutrient supplements, growth factors such as insulin, and antibiotics. By including a suitable combination of differentiation factors at the onset of differentiation, the culture will rapidly produce cells more committed to the oligodendrocyte lineage.

Expanding Oligodendrocyte Lineage Cells

As an optional step before using the cells for a desired purpose, the user of this invention may want to increase the number of oligodendrocyte lineage cells by causing them to proliferate further in culture.

This can be accomplished by culturing the cells in a nutrient medium in the presence of one or more mitogens. Exemplary are members of the family of fibroblast growth factors, such as FGF-2 (basic FGF), and FGF-4. Also exemplary is epidermal growth factor (EGF), functional homologs, and other factors that bind the EGF receptor. Other candidate growth factors are platelet-derived growth factor (PDGF), insulin-like growth factor (IGF), and factors that elevate cyclic AMP levels, such as forskolin.

In the presence of such mitogens, differentiation factor initiators such as retinoic acid can be withdrawn. Since mitogens cause cells to grow non-specifically, it is often beneficial to continue including oligodendrocyte-specific differentiation factors in the medium, to maintain preferential growth of oligodendrocyte lineage cells. Preferential growth of oligodendrocytes can also be assisted by adjusting the balance of mitogens in the culture. For example, EGF maintains ectoderm cells but not fibroblasts, which may die when FGF is no longer present. Once the cells that depend strictly on FGF have been eliminated, then FGF can be added back into the culture to accelerate growth of the desired cell type.

As another optional step in preparing the cells, the user of this invention may wish to separate oligodendrocyte lineage cells from other cell types that may be present in the culture. Various separation procedures are contemplated, such as antibody or lectin mediated adherence or sorting for cell surface markers. Suitable phenotypic markers for both positive and negative selection are listed below. Also contemplated are sorting of oligodendrocyte lineage cells using promoter-reporter plasmids, constructed with tissue-specific promoters such as those for UDP-galactose ceramide galactosyltransferase (CGT), 2',3'-cyclic nucleotide 3'-phosphodiesterase (CNP), NG2 proteoglycan, NCAM, myelin basic protein (MBP), or various myelin-associated proteins; linked to a reporter gene such as alkaline phosphatase, green fluorescent protein, or luciferase.

It has been discovered that oligodendrocyte lineage cells can be separated from other cells that propagate in the presence of oligodendrocyte differentiation factors in a more simple fashion by adhering the cells to a suitable substrate. Oligodendrocytes bear cell-specific carbohydrates and cell-surface receptors, and will preferentially adhere to the conjugate ligand. In particular, oligodendrocytes can be separated by adherence to certain basement membrane components, such as laminin, gelatin, or Matrigel®, a commercially available extracellular matrix preparation from Engelbreth-Holm-Swarm tumor cells that gels at room temperature to form a reconstituted basement membrane (Example 1). Once oligodendrocytes have adhered to the matrix (a few hours to a few days), other cell types can be washed away, and the adherent cells recovered, for example, by brief trypsin digestion. Besides enriching for the desired cell type, this procedure has the advantage of breaking up larger agglomerates of cells for ease of further manipulation.

Effectiveness of separation procedures can be determined by measuring enrichment for the markers listed below. Once the oligodendrocytes have been purified in this fashion, they can be expanded further in the presence of mitogens as already described, matured as described in the following section, or formulated in a manner suitable for ultimate use.

Further Maturation

When desired, the cells of this invention can be further matured beyond the replicative phase into a functional phenotype. This is may be done to characterize the potential of the progenitors, or obtain end-stage cells for therapeutic or drug screening purposes.

Maturation is effected by changing the growth conditions in a manner that inhibits further proliferation of the precursor phenotype. For example, the cells can be plated onto a substrate such as poly-L-lysine that promotes emergence of the mature phenotype. Alternatively or in addition, one or more of the growth factors used to expand the cells is withdrawn. Factors that enhance maturation can be included in the maturation medium, such as ciliary neurotrophic factor (CNTF), and other agonists of the CNTF receptor. Once the cells have reached the desired maturity, they can be harvested from culture (for example, using trypsin or collagen) and formulated for analysis or ultimate use.

Characteristics of Differentiated Cells

Cells can be characterized according to a number of phenotypic criteria. The criteria include but are not limited to microscopic observation of morphological features, detection or quantitation of expressed cell markers, functional criteria measurable in vitro, and behavior upon infusion into a host animal.

Phenotypic Markers

Differentiated cells of this invention can be characterized according to whether they express phenotypic markers characteristic of oligodendrocytes. Classic immunocytochemical markers for oligodendrocyte cells that may be present depending on the maturity of the cell population are the following:

NG2, a chondroitin sulfate proteoglycan expressed by macrophages and oligodendrocyte progenitors galactocerebroside (GalC), a marker for committed oligodendrocytes myelin basic protein (MBP), a marker of mature myelin and myelin-producing cells Other useful markers expressed by oligodendrocyte lineage cells include the following:

PDGFRα, a membrane receptor for PDGF, expressed by oligoprogenitors, oligodendrocytes, and other cell types TRα1, an nuclear receptor for thyroid hormone, expressed by oligoprogenitors, oligodendrocytes, neurons, and other cell types myelin proteolipid protein, a component of myelin that is expressed on oligodendrocytes and glial precursors the epitope defined by O4 antibody, a marker for oligodendrocytes, astrocytes, and their precursors vimentin, a fibroblast-type filament protein that marks astrocyte precursors (often negative on oligodendrocytes)

glial fibrillary acidic protein (GFAP), a marker for astrocytes (negative on oligodendrocytes)

A2B5, an epitope expressed on type II astrocytes, glial progenitors, oligodendrocyte progenitors, and pancreatic β cells the epitope recognized by RIP antibody, which stains oligodendrocytes and their processes, and coincides with myelinated axons in both the spinal cord and the cerebellum Transcription factors expressed at various times during the pathway of oligodendrocyte differentiation include the following:

Olig1, a helix-loop-helix (HLH) family transcription factor, expressed by oligoprogenitors, motor neuron progenitors, and kidney cells Olig2, another HLH family transcription factor, expressed by oligoprogenitors, motor neuron progenitors, and pineal gland Sox10, a Sox family transcription factor, expressed by oligoprogenitors, oligodendrocytes, Schwann cells, neural rest, cochlea, prostate, and melanocytes Nkx2.2, a Hox family transcription factor, expressed by oligoprogenitors, oligodendrocytes, neuronal progenitors, pancreatic α and β cells Pax6, an HLH family transcription factor, expressed by oligoprogenitors, neuronal progenitors, pancreatic α and β cells, lens retina, pituitary, liver, and spleen Useful markers for other cell types include the following:

neuronal nuclear antigen (NeuN), a marker of neuronal maturation (normally negative in oligodendrocyte lineage cells)

class III beta-tubulin (TuJ1), another marker of neuronal cells microtubule associated protein 2 (MAP-2), a marker for CNS cells (may be positive)

SSEA-4, Oct-4, and telomerase reverse transcriptase (TERT), markers for undifferentiated pPS cells (negative on oligodendrocytes and their precursors)

Tissue-specific markers can be detected using any suitable immunological technique-such as flow immunocytochemistry for cell-surface markers, or immunohistochemistry (for example, of fixed cells or tissue sections) for intracellular or cell-surface markers. A detailed method for flow cytometry analysis is provided in Gallacher et al., Blood 96:1740, 2000. Expression of a cell-surface antigen is defined as positive if a significantly detectable amount of antibody will bind to the antigen in a standard immunocytochemistry or flow cytometry assay, optionally after fixation of the cells, and optionally using a labeled secondary antibody or other conjugate to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for particular markers can be obtained from public databases such as GenBank. For example, myelin galactolipid biosynthetic enzyme UDP-galactose ceramide galactosyltransferase (CGT, GenBank Accession No. AH006651) is the enzyme that catalyzes the final step in the synthesis of GalC.

To facilitate use in research or therapy, it is often beneficial to maximize the proportion of cells in the population that have the characteristics of oligodendrocytes or their precursors. As illustrated in the Example section below, it is possible to obtain populations of cells that are anywhere from at least about 20%, to over about 60%, 80%, 90%, 95%, or even 98% oligodendrocyte precursors or mature cells (or a mixture of both), identified as being positive for one, two, three, or more of any of the phenotypic markers characteristic of such cells, as illustrated above.

For therapeutic applications relating to reconstitution of neural function, it is often desirable to minimize the ability of the cell population to form other cell types—particularly undifferentiated pPS cells, and cells of non-ectodermal lineage. Depending on the application, it may also be advantageous to minimize the proportion cells of the neuronal lineage and their committed precursors, cells of the astrocyte lineage and their committed precursors, and common precursors for glial cells or all types of neural cells. In certain embodiments, oligodendrocyte populations according to this invention have less than ~1%, 0.2%, or 0.05% contamination with these other types of cells.

The skilled reader will already appreciate morphological features that are characteristic of oligodendrocyte lineage cells. Oligodendrocyte precursors sometimes take a bipolar shape, having two processes extending off opposite poles from the central body. They may also take the form of relatively flat cells, bearing many of the same markers and other characteristics of oligodendrocytes. They are distinguishable from other cells (like fibroblasts) by relatively slow growth rates and dependence on extracellular matrix and soluble factors. Bipolar and flat cells may be interconvertable, depending on the presence or absence of growth factors (such as EGF, bFGF) that promote predominance of flat cells. Precursor populations of this invention may comprise at least ~20%, 40%, 60%, 80% or more of the bipolar or the flat cell phenotype.

Upon differentiation to more mature oligodendrocytes, the number and complexity of the processes will typically increase. The processes may appear to have myelin webbing in between, which wrap around individual axons to form myelin sheath that promotes neural transmission along the axon.

Genotypic Features

When derived from an isolated pPS cell, or an established line of pPS cells, the oligodendrocytes of this invention can be characterized as being the progeny of the originating cell or cell line. Accordingly, the oligodendrocytes will have the same genome as the cells from which they are derived. This means that over and above any karyotype changes, the chromosomal DNA will be over 90% identical between the pPS cells and the oligodendrocytes. Oligodendrocytes that have been treated by recombinant methods to introduce a transgene or knock out an endogenous gene are still considered to have the same genome as the line from which they are derived, since all non-manipulated genetic elements are preserved.

Oligodendrocytes and pPS cells can be identified as having the same genome by standard genetic fingerprinting techniques. Possession of the same genome can also be inferred if the oligodendrocytes are obtained from the undifferentiated line through the course of normal mitotic division.

In certain industrial applications, this characteristic is a valuable feature of the oligodendrocytes of this invention. In particular, the availability of the originating pPS cells provides a further supply of genetically matched oligodendrocytes, since the pPS cells can be caused to proliferate, subdivided, and differentiated into more oligodendrocytes as required. Furthermore, the pPS cells can be differentiated into other therapeutically important lineages. For example, they can be differentiated into immunotolerizing cell populations that can help render the intended recipient tolerant to engraftment with matched oligodendrocytes (International application PCT/US01/43434, Geron Corp.).

The techniques described in this application allow large populations of oligodendrocyte lineage cells to be produced that share the same genome, by expanding the cells before or after differentiation. Populations of 108, 1010, or 1012 cells are theoretically possible. Such large populations are usually divided into separate containers suitable for further culture, drug screening, or therapeutic administration.

Certain embodiments of the invention include originating cells (such as a undifferentiated pPS cell line, or an intermediate population) in combination with differentiated cells bearing characteristics of glial cells or oligodendrocytes. The two populations may either be in the same container, in separate containers in the same facility, or in two different locations. The undifferentiated and differentiated cells may be present simultaneously or at a different time, such as when a culture of undifferentiated cells is caused to differentiate it its entirety into oligodendrocyte lineage cells, as already described.

Functional Features

For purposes of quality control, it is often desirable to characterize the features of the differentiated cells of this invention by functional criteria. Different functions may be of different relative interest depending on the intended ultimate use. For example, the cells can be assessed for their ability to remyelinate neuronal tissue in tissue culture, to repair sites of induced demyelination in vivo, or their ability to restore neurological function in an injured subject. A number of experimental models exist for determining these features, including the following non-limiting illustrations.

1. In Vitro Myelination in Coculture:

Adult dorsal root ganglion (DRG) cultures are prepared by harvesting lumbar and cervical DRG neurons from 2-3 month old female rats. The cells are triturated, centrifuged, and resuspended in DMEM F12 medium at 100,000 viable neurons per mL, and then plated onto laminin coated dishes for 4 weeks. In vitro myelination is conducted by adding ~2.5×10$^4$ oligodendrocyte lineage cells, and culturing an additional 4 weeks with daily feeding. Myelination of rodent axons by human oligodendrocytes is illustrated in Target & Blakemore, Eye 8(part 2):238, 1994.

To determine the ability of oligodendrocyte lineage cells to form myelin, the cocultures are fixed with 4% paraformaldehyde overnight and stained for GalC. Visual fields adjacent to the ganglion are selected, and scored for the number of myelin segments per field. Differentiation potential is determined by staining low-density cultures for markers such as nestin, β-tubulin III, GFAP, CNP, GalC, Ki-67 antigen, NeuN, or neurofilament 70.

Evidence for myelination of the DRG in culture generally correlates with biological efficacy of the oligodendrocytes. Ability of the cells to survive and enhance myelination or axonal regrowth in vivo can be further obtained using a suitable animal model. On the other hand, myelination in coculture will depend on the conditions of the culture, and a negative result does not exclude efficacy in vivo. The predictive value of the in vitro test can be improved by adjusting the culture conditions: for example by adding factors believed to enhance myelination, such as IGF, or a neurotrophin like NT-3.

2. Model for Chronic Demyelination:

Regions of chronic demyelination can be induced in the adult rat dorsal column (Keirstead et al., J. Neurosci. 19:7529, 1999). The spinal cord is exposed to 40 G of X-irradiation over a distance of 2 cm centered on T9 using lead shielding, which introduces nicks into the DNA of exposed cells, which causes death of the cells that are dividing. This is followed by direct intraspinal injection of ethidium bromide 2 days later at T9. Ethidium bromide is a DNA interchelating agent that kills cells exposed to it, rendering an acellular region of chronic demyelination and free of viable oligodendrocytes and astrocytes through ~60% of the area of the dorsal column.

Three days later, the animals receive transplants of oligodendrocyte lineage cells into the site of demyelination. Optionally, the cells can be prelabeled with bromodeoxyuridine (BrdU) added to the culture medium 48 h in advance. In the first instance, cells can be prepared as clusters of ~30 precursors, concentrated to a density of ~60,000 cells per μL. One μL of cells is administered into the injury site using a pulled glass micropipette of ~80 um outside diameter over ~10 min. After about 2-4 weeks, tissue samples are prepared for resin or cryostat sectioning into 1 mm transverse blocks.

Sections from the coronal face are stained with toluidine blue and analyzed for general pathology, evidence of remyelination, and cell morphology. Since the induced regions are acellular, cells present after transplantation are derived from the administered cells. Cryostat sections can be stained for markers of relevant cell types, such as GFAP (astrocytes), CNP (oligodendrocytes), RIP (oligodendrocytes), or NeuN (neurons). Ultrathin sections can also be analyzed by electron microscopy for number of myelin lamellae and cell ultrastructure. Redistribution of transplanted cells throughout demyelination, and differentiation into mature myelinating cells can be determined. Remyelination as a percentage of demyelinated axons at a level of about 25%, 50%, or 75% is evidence of increased biological efficacy.

Therapeutic capability of oligodendrocyte lineage cells can also be tested in congenital models of dysmyelination. Established models involving a mutation or defect in myelin basic protein include the shiverer mutant mouse (Roach et al., Cell 42:149, 1985), and the Long Evans shaker rat (Kwiecien et al., J. Neurocytol. 27:581, 1989; Delaney et al., Lab. Anim. Sci. 45:547, 1995). Reconstruction can be tested by intracerebroventricular or cisternal transplantation (Mitome et al., Brain 134:2147, 2001), or by administration directly into the spinal cord (Liu, McDonald et al., Proc. Natl. Acad. Sci. USA 97:6126, 2000). Formation of compact myelin in models involving a mutation or defect in MBP is directly attributable to the administered cells, since these animals are normally not capable of proper myelination, and suffer neurological deficits as a result.

3. Model for Spinal Cord Injury:

Models for SCI include contusion injuries and dorsal hemisection. For contusion injuries, the spinal course is displaced for ~0.9 mm (moderate injury) over 23 msec using a suitable spinal contusion injury device. For hemisection injuries, the dorsal half of the spinal cord is cut with a pointed scalpel blade using a stereotactic manipulator. Both procedures are followed by suitable postoperative care.

To promote migration of implanted cells and remove myelin-associated growth inhibitors, the spinal cord is optionally also demyelinated (Keirstead et al., Exp Neurol. 151:303, 1998). A 2 mm hole is produced in the center of the vertebra canal and caudal to the site of axonal injury. The exposed spinal cord is the injected with ~4 μL polyclonal anti-GalC antibody (Chemicon) at a dilution of 1:2 with 33% guinea pig complement (Harlan SeraLab) in phosphate buffered saline. The animals are transplanted with oligodendrocyte lineage cells ~24 h after injury through a pulled glass micropipette. Alternatively, a chronic injury model can be created by withholding treatment for 1-3 months. Following treatment with the cells, functional response can be recorded by video tape, and monitored on a regular basis for evidence of clinical improvement. For example, overground locomotion can be quantitated using the BBB scale, a 21-point scale based on joint movements, weight support, limb coordination, and other features (Example 2).

For histological workup, the animals can be preinjected with tracers such as biotin-labeled cholera toxin β-subunit (CTB, 4 μL of 0.1% bilaterally into sciatic nerves), or biotinylated dextran amine (BDA, 10 μL of 10% into the sensorimotor cortex). About 2 weeks later, tissue sections are prepared as in the demyelination models for location of transplanted cells and evidence of remyelination, which is distinguishable from normal myelination or partial demyelination by morphological criteria. Sections are also analyzed for axons labeled with the injected tracers, for evidence of characteristic neurite growth cones. Immunocytochemical evidence of axonal regeneration can be assessed by staining for neuronal markers such as RT97 antigen (a marker of neurofilament), serotonin (5HT), norepinephrine (NE), and calcitonin gene-related peptide (CGRP).

Genetic Modification of Oligodendrocytes

Certain oligodendrocyte precursor populations of this invention have substantial proliferation capacity. If desired, the replication capacity can be further enhanced by increasing the level of telomerase reverse transcriptase (TERT) in the cell, by either increasing transcription from the endogenous gene, or introducing a transgene. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999.

Telomerase expression can be increased in undifferentiated pPS cells, which can then be differentiated into oligodendrocytes according to this invention. Alternatively, the pPS cells can be differentiated into oligodendrocyte precursors, and then transfected to increase TERT expression. Genetically altered cells can be assessed for TERT expression by RT-PCR, telomerase activity (TRAP assay), immunocytochemical staining for TERT, or replicative capacity, according to standard methods. Other methods of immortalizing cells are also contemplated for certain applications, such as transforming the cells with DNA encoding myc, the SV40 large T antigen, or MOT-2 (U.S. Pat. No. 5,869,243, International Patent Applications WO 97/32972 and WO 01/23555).

If desired, the cells of this invention can be prepared or further treated to remove undifferentiated cells in vitro, or to safeguard against revertants in vivo. One way of depleting undifferentiated stem cells from the population is to transfect the population with a vector in which an effector gene under control of a promoter that causes preferential expression in undifferentiated cells—such as the TERT promoter or the OCT-4 promoter. The effector gene may be a reporter to guide cell sorting, such as green fluorescent protein. The effector may be directly lytic to the cell, encoding, for example, a toxin, or a mediator of apoptosis, such as caspase (Shinoura et al., Cancer Gene Ther. 7:739, 2000). The effector gene may have the effect of rendering the cell susceptible to toxic effects of an external agent, such as an antibody or a prodrug. Exemplary is a herpes simplex thymidine kinase (tk) gene, which causes cells in which it is expressed to be susceptible to ganciclovir (U.S. Pat. No. 6,576,464 B1). Alternatively, the effector can cause cell surface expression of a foreign determinant that makes any cells that revert to an undifferentiated phenotype susceptible to naturally occurring antibody in vivo (U.S. 2003-0032187 A1).

The cells of this invention can also be genetically altered in order to enhance their ability to be involved in tissue regeneration, or to deliver a therapeutic gene to the subject being treated. A vector is designed using the known encoding sequence for the desired gene, operatively linked to a promoter that is either constitutive (such as the CMV promoter) or specifically active in cells of the oligodendrocyte lineage cells (such as the promoter for myelin basic protein). Various transgenes may be expressed according to this strategy, such as those that enhance oligodendrocyte growth, activate remyelination, or promote axon regeneration. Exemplary are genes encoding nerve growth factors (U.S. Pat. Nos. 5,885,584 and 6,268,340).

Use of Oligodendrocytes in Research and Clinical Therapy

This invention provides a method to produce large numbers of oligodendrocytes for a variety of important research, development, and commercial purposes.

The cells of this invention can be used to prepare a cDNA library relatively uncontaminated with cDNA preferentially expressed in cells from other lineages. The differentiated cells of this invention can also be used to prepare monoclonal or polyclonal antibodies that are specific for markers of oligodendrocytes and their derivatives, according to standard methods.

Of particular interest are use of the compositions of this invention for drug development and clinical therapy.

Drug Screening

The cells of this invention can be used to screen for factors (such as solvents, small molecule drugs, peptides, polynucleotides) or environmental conditions (such as culture conditions or manipulation) that affect the characteristics of both oligodendrocyte precursors and mature oligodendrocytes.

In one example, pPS cells (undifferentiated or initiated into the differentiation paradigm) are used to screen factors that promote maturation into oligodendrocytes, or promote proliferation and maintenance of oligodendrocytes in long-term culture. For example, candidate maturation factors or growth factors are tested by adding them to cells in different wells, and then determining any phenotypic change that results, according to desirable criteria for further culture and use of the cells. This can lead to improved derivation and culture methods not only for pPS derived oligodendrocytes, but also for oligodendrocytes and their progenitors isolated from primary neural tissue.

Other screening methods of this invention relate to the testing of pharmaceutical compounds for a potential adverse effect on oligodendrocyte growth, development, or toxicity. This type of screening is appropriate not only when the compound is designed to have a pharmacological effect on oligodendrocytes themselves, but also to test for oligodendrocyte-related side-effects of compounds designed for a primary pharmacological effect elsewhere.

Other screening methods relate to the use of oligodendrocytes to measure the effect of small molecule drugs that have the potential to affect oligodendrocyte activity in their role of myelinating axons. To this end, the cells can be combined with test compounds in vitro, and the effect of the compound on myelin related activities is determined—for example, expression of myelin-associated components, such as myelin basic protein; formation of myelin sheaths detectable histologically, and the ability to myelinate neighboring axons in cocultures with neuronal cells.

For general principals of drug screening, the reader is referred to U.S. Pat. No. 5,030,015, and to the textbook In vitro Methods in Pharmaceutical Research, Academic Press 1997. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Oligodendrocytes in Clinical Therapy

This invention provides for the use of oligodendrocyte precursor cells and their derivatives to retain or restore neural function in a patient in need of such therapy. In particular, the cells of this invention may be administered in order to remyelinate neuronal tissue, or otherwise provide support for the maintenance or regeneration of neural networks. Without implying any limitation, the administered cells may have the effect of stabilizing or improving the function of neurons already in place, or assist neurons in forming new connections with each other or the tissues they control.

The nature of the pharmaceutical composition will depend in part on the condition to be treated. In some instances, it may be appropriate to formulate the composition with precursor cells (positive for NP2 or GalC) having good replicative capacity and resilience to manipulation. In other instances, it may be appropriate to formulate the composition with more mature cells (positive for GalC or MBP) to provide more immediate myelination capacity.

It has been discovered that relatively disperse populations of oligodendrocyte lineage cells can be obtained easily from pPS derived cells by adhering large aggregates that form in suspension culture to a suitable matrix, such as Matrigel®. The cultured cells are plated on the substrate for a few hours to a few days, and non-adherent cells are removed. Oligodendrocyte lineage cells are then recovered by a suitable chemical or mechanical means, such as brief enzymatic digestion followed by trituration. Monodisperse populations or clusters no more than ~30 cells are believed to have advantages in terms of cell manipulation, storage characteristics, and ability to provide a beneficial effect upon administration. The cells are typically washed, and then suspended in a pharmaceutically compatible medium at a concentration suitable for administration of an effective dose so as to retain the cells at the disease site (say, 20,000 to 100,000 cells per μL, scaled by the volume of the treatment area).

Patients are prepared according to the usual procedures for neurological adaptive therapy. The patients may be treated to prevent rejection using standard immunosuppressive therapy, such as Cyclosporin A. Alternatively or in addition, they may be specifically tolerized to the allotype of the oligodendrocytes using hematopoietic cells or undifferentiated cells prepared from the same pPS cell line (WO 02/44343; WO 03/050251). In some instances, it may be beneficial to transiently demyelinate neurons at the injury site, to improve access of the administered cells or remove factors that could inhibit remyelination. One means to accomplish this is to administer to the local environment complement-fixing antibodies to one or more epitopes on the myelin sheath, such as GalC, O4, or myelin associated glycoprotein. See Keirstead et al., Brain Res. Bul. 44:727, 1997; and Canadian Patent 2,253,078. The differentiated cells of this invention are then administered in one or more doses at or around the site where myelination or regeneration of neurological function is desired.

The subject then receives supportive post-operative care, and is monitored for graft acceptance or regeneration of neurological function. Where appropriate, patients may be concurrently treated with other means believed to restore oligodendrocyte function, such as Fampridine-SR (4-aminopyridine). Histological samples can be analyzed by immunocytochemistry for relevant markers as already described, and assessed for functional events, such as axon remyelination, and neurite sprouting caused by the presence of the administered cells. The patients can be monitored for maintenance or improvement in their clinical condition, according to the typical pathological features of their disease, and assessment of function, for example, on the expanded disability status scale (EDSS).

Conditions suitable for treatment with the compositions of this invention include but are not limited to conditions involving progressive demyelination, and trauma of the central nervous system where the ability to maintain or produce myelin may either contribute to healing, or help prevent further deterioration.

Multiple Sclerosis is a slowly progressive disease characterized by disseminated patches of demyelination in the brain and spinal cord. Plaques of demyelination, with destruction of oligodendroglia and perivascular inflammation, occur throughout the CNS, primarily in the white matter (especially in the cervical and dorsal regions), the optic nerves, and periventricular areas. Tracts in the midbrain, pons, and cerebellum, and gray matter in the cerebrum and spinal cord are also affected.

Acute disseminated encephalomyelitis (postinfectious encephalomyelitis) is characterized by perivascular CNS demyelination, which can occur spontaneously but usually follows a viral infection or viral vaccination. Chronic inflammatory demyelinating polyradiculoneuropathy (CIDP) is characterized by interstitial and perivascular infiltration of the endoneurium with inflammatory T cells and macrophages, leading to segmental demyelination of peripheral nerves. HTLV-associated myelopathy is a slowly progressive spinal cord disease characterized by spastic weakness of both legs. Some peripheral neuropathies, such as Guillain-Barre syndrome, are also characterized by demyelination.

Congenital metabolic disorders (such as phenylketonuria and other aminoacidurias; Tay-Sachs, Niemann-Pick, and Gaucher's diseases; Hurler's syndrome; Krabbe's disease and other leukodystrophies) affect the developing myelin sheath in the CNS, and may cause permanent widespread neurologic deficits. Adrenoleukodystrophy and adrenomyeloneuropathy are X-linked recessive metabolic disorders characterized by adrenal gland dysfunction and widespread demyelination of the nervous system. Pelizaeus-Merzbacher disease is a condition where patents do not form myelin because of a point mutation in the proteolipid protein gene. Leber's hereditary optic atrophy and related mitochondrial disorders are characterized primarily by bilateral loss of central vision.

Any acute or long-term abnormalities caused by trauma to the CNS may be considered for treatment, as well as conditions related to loss of myelin through anoxia and ischemia. Included in this category are conditions related from stroke or traumatic brain injury.

Spinal cord injuries of various kinds, causing paraplegia or incomplete motor function at any level, are prime candidates for treatment using the cells of this invention. Depending on the nature and accessibility, injuries to the cervical, lumbar, thoracic, and sacral spine may all derive an improvement or stabilization of their condition. Acute injuries causing complete or incomplete loss of SC function can be treated simultaneously or soon after decompression surgery. Chronic conditions can be treated or retreated whenever desirable. The cells can be administered at or near the site of the injury by surgery, endoscopy, or percutaneous injection, using a needle, cannula, or other suitable device. If warranted, the electrophysiological effect can be determined using an evoked potentials test. The patients can also be assessed for clinical improvement in the motor and sensory pathway by criteria such as the American Spinal Injury Association (ASIA) motor score, and the Ferrans and Powers Quality of Life Index (QLI).

As always, the ultimate responsibility for patient selection, mode of administration, and monitoring of rehabilitation is the responsibility of the managing clinician.

For purposes of commercial distribution, oligodendrocytes of this invention are typically supplied in the form of a pharmaceutical composition comprising an isotonic excipient, and prepared under conditions that are sufficiently sterile for human administration. This invention also includes a reagent system, comprising a set or combination of cells that exist at any time during manufacture, distribution, or use. The cell sets comprise any combination of two or more cell populations described in this disclosure, exemplified but not limited to a type of differentiated pPS-derived cell (glial cells, oligodendrocytes, their precursors and subtypes, and so on), in combination with undifferentiated pPS cells or other differentiated cell types, sometimes sharing the same genome. Each cell type in the set may be packaged together, or in separate containers in the same facility, or at different locations, at the same or different times, under control of the same entity or different entities sharing a business relationship.

For general principles in medicinal formulation of cell compositions, the reader is referred to Cell Therapy: Stem Cell Transplantation, Gene Therapy, and Cellular Immunotherapy, by G. Morstyn & W. Sheridan eds, Cambridge University Press, 1996; and *Cell Transplantation for Neurological Disorders*, T. B. Freeman et al. eds., Humana Press 1998. The cells may be packaged in a device or container suitable for distribution or clinical use, optionally accompanied by information relating to the storage of the cells or their use as a medicament to treat the clinical conditions referred to above, or for any other worthwhile purpose.

The following examples are provided as further non-limiting illustrations of particular embodiments of the invention.

EXAMPLES

Example 1

Differentiation of hES Cells into Oligodendrocytes

Human embryonic stem (hES) cells of the H7 and H1 lines were propagated in the undifferentiated state in feeder-free conditions on a Matrigel® substrate in knockout (serum-free) medium conditioned by primary mouse feeder cells and containing added bFGF (WO 99/20741; WO01/51616, Geron Corp).

The hES cells were differentiated into cells of the oligodendrocyte lineage according to the following scheme:

TABLE 1

Oligodendroprogenitor Production from hES cells

| Day: | 1 | 2 | 3-10 | 11-15 | 15-28 | 28 | 29-35 | 35-36 | 37-41 | 42 |
|---|---|---|---|---|---|---|---|---|---|---|
| Culture conditions: | Suspension culture | Add retinoic acid (RA) | Full strength medium | Remove RA | Remove bFGF | Plate on Matrigel® | Expand cells | Plate on PLL-Laminin | Remove growth factors | Fix cultures |
| Medium: Additives: | TR bFGF 4 ng/mL | TR bFGF 4 ng/mL; RA 10 µM | GRM RA 10 µM | GRM bFGF 2 ng/mL; EGF 20 ng/mL | GRM EGF 20 ng/mL | GRM EGF 20 ng/mL | GRM EGF 20 ng/mL | GRM bFGF 2 ng/mL; EGF 20 ng/mL | GRM — | GRM — |

GRM is Glial Restriction Medium (see Table 2).
Transition medium (TR) is made as a 1:1 mixture of GRM and conditioned medium for making hES cells.

TABLE 2

Ingredients of Glial Restriction Medium (GRM)

| Component | Manufacturer (catalog) | Stock concentration | Final concentration | Quantity |
|---|---|---|---|---|
| DMEM:F12 (base medium) | Gibco (10565-018) | — | — | 500 mL |
| B27 supplement | Gibco (17504-044) | 50 x | 1:50 | 10 mL |
| Insulin | Sigma (I-1882) | 25 mg/mL | 25 µg/mL | 1 µL/mL |
| Progesterone | Sigma (P-6149) | 65 µg/mL | 65 ng/mL | 1 µL/mL |
| Putrescine | Sigma (P-6024) | 10 mg/mL | 10 µg/mL | 1 µL/mL |
| Sodium selenite | Sigma (S-9133) | 0.1 mg/mL | 100 ng/mL | 1 µL/mL |
| Transferrin (Holotransferrin) | Sigma (T-8158) | 50 mg/mL | 50 µg/mL | 1 µL/mL |
| T3 (triiodothyronine) | Sigma (T-67407) | 40 µg/mL | 40 ng/mL | 1 µL/mL |

The differentiation protocol was conducted as follows:

Day 1: Collagenase IV (Gibco 17101-015) was used to dissociate the ES colonies from the adherent substrate and colonies were placed in low adherent 6 well plates (Corning 3471) in TR with 4 ng/mL bFGF (Gibco 13256-029). Penicillin-Streptomycin (Gibco 10378-016) was used for 3 days only at the beginning of differentiation protocol.

Day 2-10: Cells were cultured with retinoic acid (RA; all-Trans-retinoic acid, Sigma 223018), 10 µM, feeding daily for a total of 8 days. The RA stock solution was prepared in DMSO at a concentration of 6 mg/mL (approx. 0.02 M).

From day 3, the medium was replaced with GRM, and no more bFGF was added to the culture. Medium was replaced every day. During feeding, light was dimmed to minimum because RA is light sensitive. Medium from the wells containing the ES cell aggregates was collected in 15 mL tubes. After a short centrifugation at low speed (800 rpm, 1 minute), the supernatant was aspirated and fresh medium was added. Gentle pipetting up and down (2-3 times) assured a homogenous distribution of 4 mL in each well of the 6 well plates.

Day 10 to 15: After day 10, EGF (Sigma E9644) at a concentration of 20 ng/mL and bFGF 2 ng/mL was added during the daily feeding.

Day 15 to 21: bFGF was suppressed from culture medium, while EGF was continued at a concentration of 20 ng/mL.

After day 21: New aggregates/clusters with neural characteristics could be generated even after day 42 by maintaining the GRM medium with 20 ng/mL EGF.

To select for these neurospheres, the entire culture was transferred on the 28$^{th}$ day of the differentiation procedure, without using any dissociation protocol, on Matrigel® coated 6-wells plates (Matrigel® 1:30, BD Bioscience 356231) for 12-20 hours (overnight). The next day, after a gentle shake of the culture, only the neurospheres remained adherent, and the rest of culture was replaced with fresh GRM medium.

On day 35, the neural aggregates were plated on poly-L-lysine (Sigma P2636) and laminin coated four chamber imaging slides (Nalgene-Nunc International 154917). A short treatment (5 min) with Trypsin-EDTA was used to dissociate the cell agglomerations. The cells were grown for 7 days on the PLL-laminin, during which cultures were fed every other day.

On day 42, the cultures were fixed using paraformaldehyde, and the cells were characterized by immunohistochemistry. Markers used: NeuN, Galactocerebroside (GalC), Map2, O4, Vimentin, GFAP.

Results are shown in the accompanying phase inverted photomicrographs.

Figure 1:
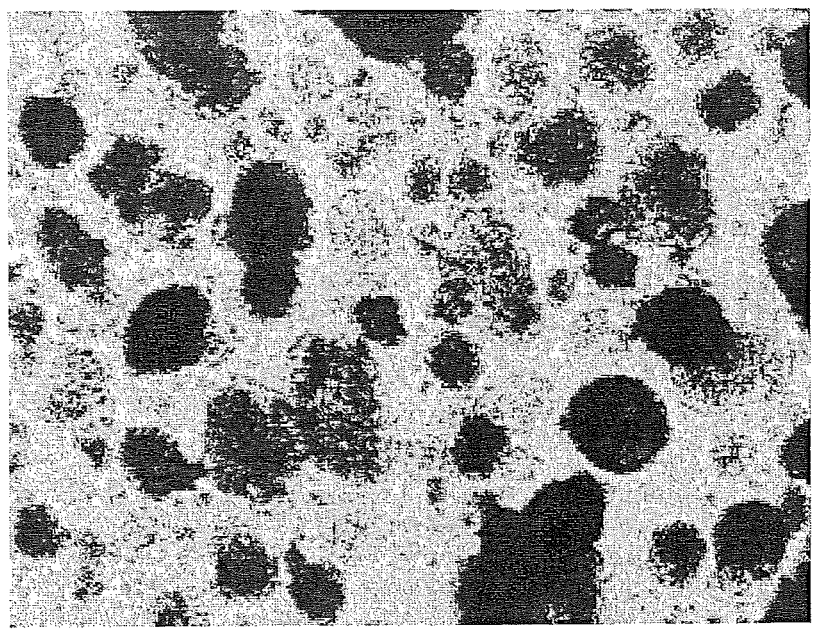
FIG. 1 is a phase contrast image taken using an inverted microscope, showing human embryonic stem (ES) cells that have been cultured 2 days in suspension in a medium containing basic FGF, and oligodendrocyte differentiation factors.

FIG. 1 shows embryoid bodies cultured for two days in suspension in transition medium (50% glial precursor medium).

Figure 2:
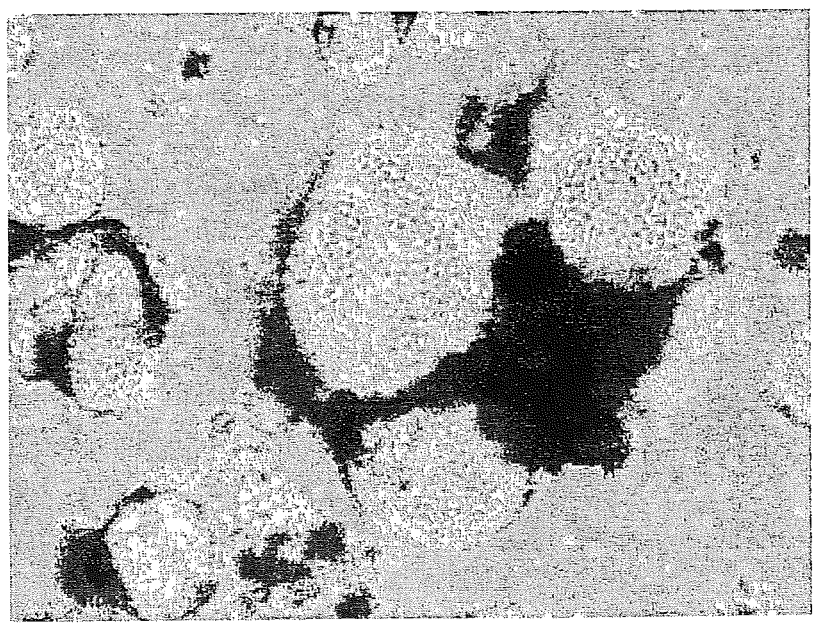
FIG. 2 shows the cells after culturing for 7 days with retinoic acid. Large clear spheres of cells were present, representing 80-90% of the cells in the culture.

FIG. 2 shows spheres on day 7 of differentiation, at the end of culturing in retinoic cid. From day 3 onwards, clear spheres began appearing in the suspension culture. By day 7, these spheres constituted 80-90% of the cells in the culture.

Figure 3:
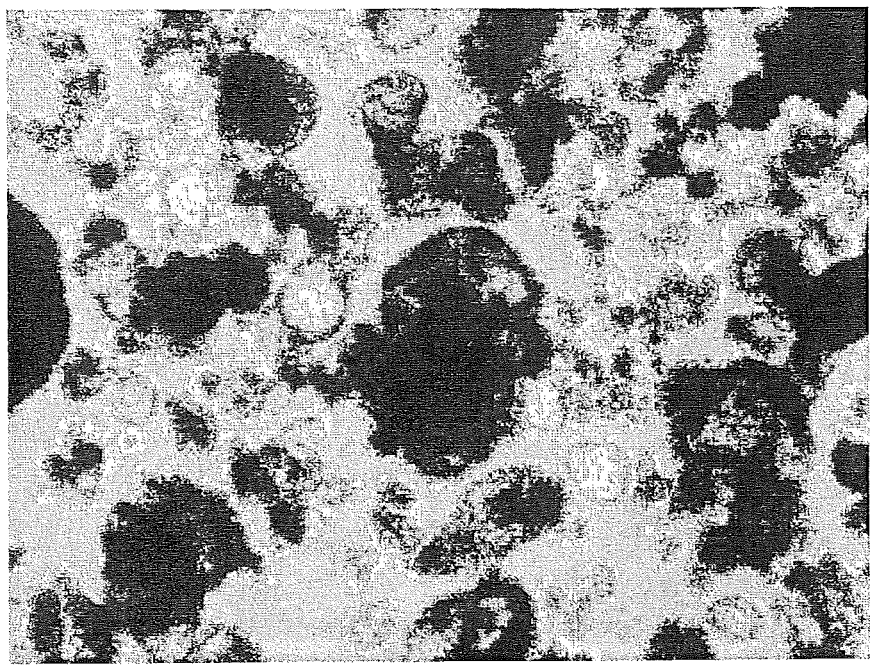
FIG. 3 shows what happens after retinoic acid is removed, and the cells are maintained in the presence of a low concentration of FGF.

FIG. 3 shows collapse of spheres after suppression of RA treatment. Some of the vesicles continued to grow by addition of cells to the inside and outside of the sphere; the cell conglomerations took a dark shaded spherical shape. The spheres collapsed in presence of 20 ng EGF alone.

However, the spheres could be maintained by adding a low concentration of bFGF. Some of the spheres continued to grow by addition of new cells, resulting a spherical shaped, dark shaded cell conglomeration. Some small spheres with thick walls continued to grow, but completely disappeared after few days. Accordingly, the bFGF was retained in the culture at low concentration (2 ng/mL) for 5 days, and the spheres continued to grow by adding layers.

FIG. 4 shows the changes appearing after bFGF was removed. Most of the cell conglomerates started to dissociate and the entire culture medium was flooded with single cells and small clusters. At the same time, new bright yellow spheres were observed (arrows).

FIG. 5 shows that the bright-yellow spheres (arrows) were selectively maintained as the culture continued. New spheres appeared every day, some budding from other spheres, some from the isolated cell mass and some from the dark cell agglomerations.

On day 28, the entire culture was adhered to a Matrigel® substrate overnight. Only the neural committed spheres adhered to substrate, while the rest of the culture continued to float.

terstained using hematoxin. (First panel 20× magnification; second panel 40× magnification).

At least about 95% of the cells in the field show staining for GalC, a marker of mature oligodendrocyte lineage cells.

FIG. 8 shows a higher magnification of ES-derived oligodendrocytes stained for GalC (60× magnification). At least ~10% or 20% of the cells have morphological characteristics of oligodendrocytes: specifically, numerous processes with webbing in between that is evocative of myelin sheets.

Example 2 hES Derived Oligodendrocytes Cause Remyelination and Neural Sprouting In Vivo

For this example, hES cells form the H7 line were differentiated into oligodendrocyte precursor cells for transplantation using a similar strategy as in Example 1, with some refinements. The formula for GRM was the same, except that the progesterone concentration was recalculated as 65 ng/mL. EGF was included in the culture from the outset, and bFGF was withdrawn after Day 2.

TABLE 3

Oligodendroprogenitor Production from hES cells

| Day: | 1 | 2 | 3-9 | 10-15 | 15-28 | 28-35 |
|---|---|---|---|---|---|---|
| Culture conditions: | Suspension culture | Add retinoic acid (RA) | Full strength medium | Remove RA | Remove bFGF | Plate on plastic 1 hour; Plate on Matrigel ® overnight |
| Medium: | TR | TR | GRM | GRM | GRM | GRM |
| Additives: | bFGF 4 ng/mL EGF 20 ng/mL | bFGF 2 ng/mL EGF 20 ng/mL RA 10 µM/mL | EGF 20 ng/mL RA 10 µM/mL | bFGF 2 ng/mL EGF 20 ng/mL | EGF 20 ng/mL Feed every other day (MWF); non-adherent; complete media replacement | EGF 20 ng/mL |

FIG. 6 shows migration and branching of the glial committed neural precursors from the spheres 2-3 days after plating on Matrigel®. The smaller colonies formed a circle by longitudinal division of individual cells, while the large ones showed a star shape migration with long processes. More migrating cells appeared after a few days of growth on Matrigel®.

After a week, the culture was dissociated from Matrigel® using Trypsin, and then plated on poly-L-lysine and Laminin (Gibco 12163-010) coated Nunc imaging chambers at low density for further characterization. The plated cells adopted characteristically oligodendrocyte shapes after 3-4 days of growth on Laminin substrate.

It was subsequently discovered that the Matrigel® selection step can be reduced to 10-20 hours. The non-adherent cells are discarded, and the adherent cells are then resuspended and expanded in the presence of FGF, EGF, and glial precursor medium. This has the advantage of producing a more disperse cell population more suited for therapeutic administration and other purposes.

FIG. 7 shows the results of this technique. After adhering to Matrigel®, the cells were expanded for 7 days, plated onto poly-L-lysine laminin, and cultured in the absence of mitogens. The cells were fixed with 4% paraformaldehyde, and blocked in 3% goat serum and 0.3% Triton-X 100® detergent. Immunocytochemistry was performed using antibody to galactocerebroside (GalC, Chemicon), followed by peroxidase-labeled anti-immunoglobulin. Nuclei were coun- In the first week, feeding was preceded by a 4-5 minute centrifugation at low speed. After spheres start to grow, feeding was done by letting the culture sediment for 5-10 minutes in the incubator in 15-50 mL conical tubes. The cells expressing adhesion factors form aggregates (spheres) and sediment faster than the non-adherent cells in single cell suspension. This increases the purity of cultures with intercellular adhesion characteristics.

FIG. 9 shows the progression of cell morphology during the differentiation scheme. (A): Undifferentiated hES cells growing in feeder-free culture on Matrigel® in mEF conditioned medium. (B): By day 3, transparent spheres grew from embryoid bodies in suspension culture in medium containing retinoic acid, indicating rapid cell diffusion. (C): Induction of neurolineage cells with retinoic acid (Stage 3) followed by commitment and expansion of oligodendrocyte precursor cells in the presence of EGF (Stage 4) was evident by the massive accumulation of yellow spheres. (D) Cells were then plated onto Matrigel® for positive selection of the desired cell type. (E, F): The size of the spheres and percentage of the culture increased as the expansion stage progressed. After preferential selection, the glial-committed progenitors could be maintained and amplified for up to 8 weeks. (G, H): Subsequent plating of the oligodendrocyte precursors onto poly-L-lysine and laminin in the absence of mitogens caused them to adopt a morphology of mature oligodendrocytes within one week.

FIG. 10 shows an immunocytochemical analysis of the mature oligodendrocytes. One week after plating, over 94% of the cells labeled with antibody to NG2, a marker of early stage glial cells (A). Eight weeks after plating, over 95% of the cells stained positively for GalC (C), O4 (D), and RIP (E). When cells were stained with anti-GFAP and counterstained with DAPI virtually all of the cells that did not label with oligodendroglial markers were GFAP positive (B).

The oligodendrocyte precursor cells were then administered to the low thoracic spinal cord of anesthetized adult Sprague Dawley rats with a moderate contusion injury of the spine induced using an Infinite Horizon™ impactor device (Precision Systems and Instrumentation, LLC).

FIG. 11 shows tissue sections obtained after administration of the cells, stained with antibody specific for human nuclear protein. The dark staining confirms that human cells survive after grafting.

FIG. 12 shows transverse sections of the area around the spinal cord, 9 weeks after transplant, stained for human nuclear protein. The animals had been treated with Cyclosporin A to prevent rejection. The cells have migrated or proliferated into the white matter.

FIG. 13 shows the results of a detailed analysis to determine whether the cell implant has an adverse effect on the site of administration. Serial sections were taken along the length of the spinal cord through the injury site of untreated and engrafted animals. Each bar shows the average cross-sectional area measured in five sections (mean±SEM). Smaller cross-sectional area near the contusion is the result of secondary enlargement following injury. The oligodendrocytes do not induce sparing, but they also do not make the injury worse. This shows that hES-derived oligodendrocytes are safe even when administered within 1 mm of a spinal cord injury.

FIG. 14 was obtained from an experiment to measure neuronal branching. Eight weeks after injury, animals were injected with BDA as an anterograde tracer of the motor cortex in the corticospinal tract. These sections were taken two weeks later. Only in animals treated with hES-derived oligodendrocytes was there evidence of axon branching— shown in the upper two panels as the darkly stained narrow lines. The branching was observed in areas of the spinal cord just above the injury.

FIG. 15 shows quantitation of the neuronal branching measured at 1 mm intervals from the site of injury and cell administration (the epicenter) (mean±SEM for 3 sections per block). Labeled axons were counted in injured animals that did not receive treatment 3 mm above the site. Treated animals had labeled axons at a significantly higher level right up to the epicenter on the rostral side of the injury. This confirms that the engrafted cells are inducing regenerative plasticity.

FIG. 16 is a series of electron micrographs of sections taken from engrafted animals, showing evidence of substantial remyelination. The thick circle in the upper left panel is a normally myelinated fiber. The rest of the axons in the field show a thin layer of myelin. The sheath to axon diameter ratio indicates that these axons are newly myelinated. The upper right panel is a higher resolution image of a newly myelinated axon. There are about 5 or 6 wraps, and an axonal tongue at the top, representing the leading edge of the oligodendrocyte. This shows that myelination of this axon is an ongoing process. The lower panel shows a thick myelin sheath being deposited by a Schwann cell. This occurs regardless of the transplant, and provides a limited degree of recovery in untreated animals. However, only the animals engrafted with the hES derived oligodendrocytes showed evidence of myelination of the sort observed in the upper panels, characteristic of oligodendrocytes.

Example 3

Phenotypic Characterization of Oligodendrocyte Lineage Cells

In this example, marker expression was followed during production of oligodendrocytes from hES line H7 according to the protocol shown in Table 4.

TABLE 4

Oligodendroprogenitor Production from hES cells

| Day: | 1 | 2 | 3-9 | 10-21 | 21-28 |
|---|---|---|---|---|---|
| Culture conditions: | Suspension culture | Add retinoic acid (RA) | Full strength medium; Remove bFGF | Remove RA | Plate on Matrigel ® |
| Medium: | TR | TR | GRM | GRM | GRM |
| Additives: | bFGF 4 ng/mL EGF 20 ng/mL | bFGF 2 ng/mL EGF 20 ng/mL RA 10 μM/mL | EGF 20 ng/mL RA 10 μM/mL | EGF 20 ng/mL Feed every other day (MWF); non-adherent; complete media replacement | EGF 20 ng/mL |

In the general application of this protocol, oligodendrocyte progenitors suitable for transplantation are obtained after the solid-phase selection step (any time after day ~23). Culturing in the final stage can occur to expand the cells as required (at least 8 weeks), by passaging once a week using trypsin.

For purposes of phenotypic analysis in this example, the cells were adapted to low-density culture using GRM containing 5% knock-out serum replacement. The presence of 5% KO-SR starting on day 21 improved the proliferation of bipolar cells when plated on Matrigel®. When the cells were plated on laminin (15 μg/mL on poly-L-lysine) at low density, the KO-SR improved cell survival and growth. Use of KO-SR earlier in the protocol did not affect the course of differentiation, as observed by the growth rate and proportion of yellow spheres.

FIG. 17 shows markers detected on undifferentiated hES cell colonies. Left side panels show in black and white the red fluorescence from antibody specific for each marker, superimposed on blue fluorescence of DAPI staining, marking the location of all cell nuclei in the field. Right side panels show the marker staining alone. Comparison of the two images allows the viewer to estimate the proportion of total cells in the field that express the marker in question.

The top row shows colonies positively labeled for SSEA-4, a marker of pluripotent cells. The bottom row shows stromal cells surrounding the colonies positively labeled for the mesodermal marker BMP4. The undifferentiated cells within each colony are BMP4 negative.

FIG. 18 shows the transient appearance of transcription factor Pax6 during differentiation (Left side: antibody plus DAPI; right side: antibody staining alone). Top row shows staining towards the center of the cluster on day 10, already regulated down in the more differentiated cells towards the periphery. Bottom row shows virtually no staining in cells sampled at day 35.

FIG. 19 shows markers detected in early-stage oligodendrocyte lineage cells, present just after removal of retinoic acid on day 10 (Left side: antibody plus DAPI; right side: antibody staining alone). Top row: the transcription factor Olig1 (83%±7%). Middle row: the transcription factor SOX10 (72%±12%). Bottom row: non-specific oligodendrocyte progenitor marker A2B5 (97%±3%).

FIGS. 20A-20B show markers predominating in the fully differentiated oligoprogenitors at day 35 (Left side: antibody plus DAPI; right side: antibody staining alone). First and second rows (20A): NG2 (chondroitin sulfate proteoglycan, a marker of oligodendrocyte precursors); Third row (20A): GalC; Fourth row (20B): O4; Fifth row (20B): Tuj1 (a marker of neurons).

The results show that at least about 80% of the cells are positive for oligodendroglial markers NG2, GalC, and O4. Cells that did not label with oligodendroglial markers were primarily positive for the neuron markers GFAP or Tuj1 (20B, bottom). Double immunocytochemistry shows that no GFAP or Tuj1 positive cell co-expressed oligodendroglial markers. Furthermore, no BMP4 or SSEA-4 could be detected, indicating that these cultures were devoid of undifferentiated cells or mesodermal lineage cells. This cell population could be caused to proliferate through at least eight subsequent passages.

Example 4 hES-Derived Oligodendrocytes Remyelinate Axons in Myelin-Deficient Animals

To demonstrate that the myelination caused by these cells in vivo was a direct effect (rather than by induction of endogenous oligodendrocytes), cells from day 28 of the differentiation protocol were transplanted into the shiverer mouse model of demyelination. Shiverer mice are homozygous for a mutation in the myelin basic protein gene located on chromosome 18 (Mbpshi/Mbpshi). This gene is duplicated and a large portion of the duplicated gene is inverted, leading to the formation of antisense RNA; this results in severe myelin deficiency throughout the CNS.

Oligodendrocyte progenitor cells were harvested from culture, washed in DMEM, concentrated, and loaded into a silicon coated Hamilton syringe. Animals were immunosuppressed in this as in all experiments with 10 mg/kg cyclosporin A. Six weeks later, the animals were sacrificed and sectioned for EM analysis.

FIG. 21 shows the results. Ultrastructurally, axons of shiverer mice are devoid of myelin or are surrounded by one or two uncompacted wraps of myelin (Upper Panel). Six weeks after transplantation of cells, electron microscopic analysis indicated multilayered compact myelin indicting the myelinogenic capability of the transplant population (Lower Panel).

Since the mice are deficient in the ability to produce myelin basic protein, the compact myelin must be produced directly by the administered oligodendrocytes, and not due to a trophic effect.

Example 5

ES-Derived Oligodendrocytes Restore Spinal Cord Function

Ability of ES-derived oligodendrocyte lineage cells to restore neurological activity was determined in a rat contusion model of spinal cord injury.

Moderate contusion injury was induced in the low thoracic spinal cord of anesthetized adult Sprague Dawley rats using an impactor device. One week after the injury, the contusion site was transplanted with 2.5×105 cells in 4 µL medium. The transplant cell population was prepared by exposing cells at Day 35 of the differentiation scheme (Example 1) for 3 min with trypsin and EDTA to render the cells non-adherent. They were then rinsed in basal medium, and concentrated to 6×104 cells per µL.

Six weeks after injury, the animals were injected with the anterograde tracer BDA (biotinylated dextran amine) into the motor cortex. Emerald green was injected into the lumbar spine to label lumbar tracts. The location of these markers was determined when the experiment was terminated at 8 weeks.

FIG. 22 shows the overground locomotion scores for each of the two groups in this experiment. The upper graph shows the results of animals subject to a 200 kiloDyne contusion; the lower graph shows results of a 250 kiloDyne contusion. The BBB scale is a 21-point scale that rates normal overground locomotion based on joint movements, weight support, limb coordination, foot placement and gait stability (Basso, Beattie, & Bresnahan, J. Neurotrauma, 12:1, 1995). (■) animals treated with ES-derived oligodendrocytes 1 week after injury (n=5); (▲) control animals receiving the same contusion but no administered cells (n=3). Mean±SEM, for assessments done blinded.

Animals engrafted with hES derived oligodendrocytes showed significantly better function (*=p<0.05), persisting for more than 5 weeks after treatment.

These results demonstrate that ES-derived oligodendrocytes help restore function in an animal model for spinal cord injury. The earlier examples show that transplanted oligodendrocytes cause neuronal sprouting, and remyelination of myelin-deficient axons. Either or both of these effects may contribute to the improved behavior observed here.

It is understood that certain adaptations of the invention are a matter of routine optimization, and can be implemented without departing from the spirit of the invention, or the scope of the appended claims.

The invention claimed is:

1. A first cell population and a second cell population, comprising:
    a) a first cell population comprising a line of undifferentiated human embryonic stem (hES) cells in a cell culture medium comprising a mitogen, a ligand for a thyroid hormone receptor, and a ligand for a retinoic acid receptor, wherein the mitogen and the ligands are present in an amount effective for differentiation of the line of undifferentiated hES cells into oligodendrocyte precursor cells; and
    b) a second cell population comprising the oligodendrocyte precursor cells which are the in vitro progeny of the line of undifferentiated hES cells, wherein the oligodendrocyte precursor cells stain with antibody specific for NG2 proteoglycan and are negative for the neuronal marker NeuN.

2. The first cell population and the second cell population of claim 1, wherein the oligodendrocyte precursor cells also express A2B5.

3. The first cell population and the second cell population of claim 1, wherein the oligodendrocyte precursor cells also express platelet-derived growth factor receptor-α (PDGFR α).

4. The first cell population and the second cell population of claim 1, wherein 20% or more of the oligodendrocyte precursor cells show a bipolar morphology characteristic of oligodendrocyte precursors.

5. The first cell population and the second cell population of claim 1, wherein implantation of the second cell population into the spinal cord of a shiverer mutant mouse causes deposition of compact myelin around neuronal axons.

6. The first cell population and the second cell population of claim 1, wherein implantation of the second cell population in or around the spinal cord in a contusion-injured rat causes improvement in overground locomotion compared with a contusion injured rat that does not receive the implantation of the differentiated cell population.

7. The first cell population and the second cell population of claim 1, wherein the mitogen is selected from the group consisting of basic fibroblast growth factor (bFGF) and epidermal growth factor (EGF).

8. The first cell population and the second cell population of claim 1, wherein the ligand for the thyroid hormone receptor is thyroid hormone triiodothyronine (T3).

9. The first cell population and the second cell population of claim 1, wherein the ligand for the retinoic acid receptor is retinoic acid (RA).

10. The first cell population and the second cell population of claim 1, wherein the mitogen is basic fibroblast growth factor (bFGF), the ligand for the thyroid hormone receptor is thyroid hormone triiodothyronine (T3), and the ligand for the retinoic acid receptor is retinoic acid (RA).

11. The first cell population and the second cell population of claim 10, wherein the concentration of thyroid hormone T3 is 20 ng/ml.

12. The first cell population and the second cell population of claim 10, wherein the concentration of RA is 10 μM.

13. The first cell population and the second cell population of claim 10, wherein the concentration of bFGF is 4 ng/ml.

14. The first cell population and the second cell population of claim 10, wherein the concentration of thyroid hormone T3 is 20 ng/ml, the concentration of RA is 10 μM, and the concentration of bFGF is 4 ng/ml.

15. The first cell population and the second cell population of claim 1, wherein the first cell population and the second cell population are in separate containers.

16. The first cell population and the second cell population of claim 1, wherein at least 80% of the cells of the oligodendrocyte precursor cells stain with antibody specific for NG2 proteoglycan.

* * * * *